(12) United States Patent
Liang

(10) Patent No.: US 11,547,659 B2
(45) Date of Patent: *Jan. 10, 2023

(54) IN SITU GEL-FORMING PHARMACEUTICAL COMPOSITIONS AND USES THEREOF FOR SINUS DISEASES

(71) Applicant: IVIEW Therapeutics, Inc., Cranbury, NJ (US)

(72) Inventor: Bo Liang, Plainsboro, NJ (US)

(73) Assignee: IVIEW Therapeutics, Inc., Cranbury, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/345,634

(22) PCT Filed: Sep. 4, 2018

(86) PCT No.: PCT/US2018/049333
§ 371 (c)(1),
(2) Date: Apr. 26, 2019

(87) PCT Pub. No.: WO2019/046844
PCT Pub. Date: Mar. 7, 2019

(65) Prior Publication Data
US 2019/0269611 A1 Sep. 5, 2019

Related U.S. Application Data

(60) Provisional application No. 62/553,806, filed on Sep. 2, 2017.

(51) Int. Cl.
*A61K 9/00* (2006.01)
*A61K 9/06* (2006.01)
(Continued)

(52) U.S. Cl.
CPC ............. *A61K 9/0043* (2013.01); *A61K 9/06* (2013.01); *A61K 9/08* (2013.01); *A61K 9/10* (2013.01);
(Continued)

(58) Field of Classification Search
None
See application file for complete search history.

(56) References Cited

U.S. PATENT DOCUMENTS 8,859,531 B2   10/2014   Lee et al.
9,700,650 B2    7/2017   Gong et al.
(Continued)

FOREIGN PATENT DOCUMENTS

CN        1698584 A      11/2005
CN      101015559 A       8/2007
(Continued)

OTHER PUBLICATIONS

Kumar et al.. "Formulation and Evaluation of pH-induced povidione iodine in situ gel for Oralthrush", J. Pharm. Sci. & Res. vol. 2(5), 2010, pp. 294-301. (Year: 2010).*
(Continued)

*Primary Examiner* — Kyung S Chang
(74) *Attorney, Agent, or Firm* — Weisun Rao; Sunyong Tang; Venture Partner, LLC

(57) ABSTRACT

The present invention provides pharmaceutical compositions comprising an antiseptic and a steroid, useful for treating a clinical symptom in a patient's airway (e.g., nose, lung, and sinus), wherein a gel containing the antiseptic is formed in situ upon instillation of the compositions onto a body cavity of a subject, as well as methods for using the same.

28 Claims, 13 Drawing Sheets

Figure 1:
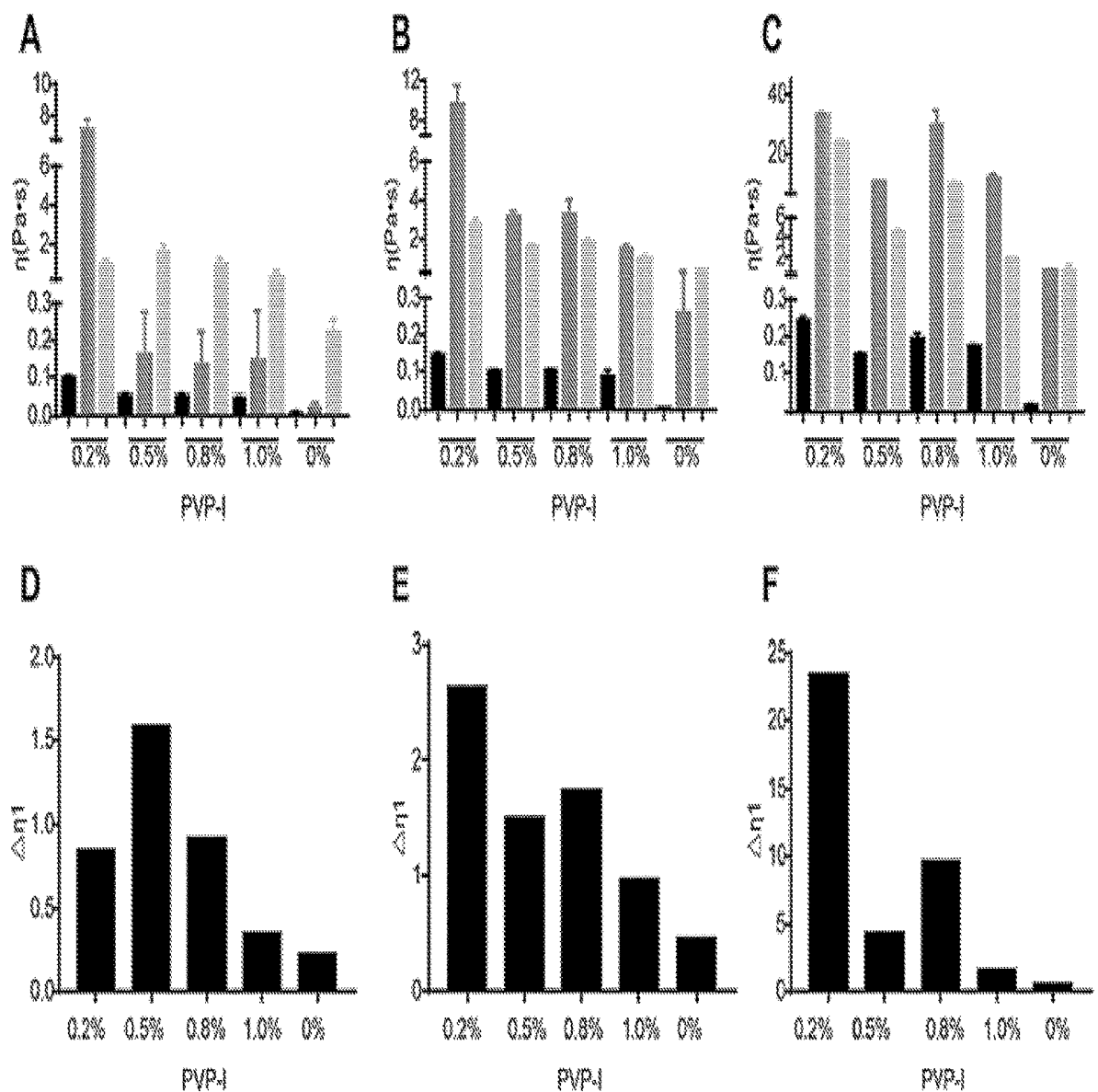

(51) Int. Cl.
*A61K 31/155* (2006.01)
*A61K 31/555* (2006.01)
*A61K 31/565* (2006.01)
*A61K 31/58* (2006.01)
*A61K 33/18* (2006.01)
*A61M 11/00* (2006.01)
*A61K 47/02* (2006.01)
*A61K 47/10* (2017.01)
*A61K 47/18* (2017.01)
*A61K 47/36* (2006.01)
*A61K 31/56* (2006.01)
*A61K 9/10* (2006.01)
*A61K 9/08* (2006.01)
*A61P 11/02* (2006.01)
*A61P 31/02* (2006.01)
*A61K 45/06* (2006.01)
*A61K 47/32* (2006.01)

(52) U.S. Cl.
CPC .......... *A61K 31/155* (2013.01); *A61K 31/555* (2013.01); *A61K 31/56* (2013.01); *A61K 31/565* (2013.01); *A61K 31/58* (2013.01); *A61K 33/18* (2013.01); *A61K 45/06* (2013.01); *A61K 47/02* (2013.01); *A61K 47/10* (2013.01); *A61K 47/18* (2013.01); *A61K 47/36* (2013.01); *A61M 11/007* (2014.02); *A61P 11/02* (2018.01); *A61P 31/02* (2018.01); *A61K 47/32* (2013.01)

(56) References Cited

U.S. PATENT DOCUMENTS

| | | |
|---|---|---|
| 2007/0110788 A1 | 5/2007 | Hissong et al. |
| 2009/0263345 A1* | 10/2009 | Capriotti .............. A61K 9/0046 424/78.07 |
| 2010/0016267 A1 | 1/2010 | Theeuwes et al. |
| 2013/0045182 A1* | 2/2013 | Gong .................. A61L 24/0031 424/93.1 |
| 2014/0219949 A1 | 8/2014 | Liang et al. |
| 2017/0266294 A1 | 9/2017 | Baldwin et al. |

FOREIGN PATENT DOCUMENTS

| | | |
|---|---|---|
| CN | 102078286 A | 6/2011 |
| CN | 102078325 A | 6/2011 |
| CN | 102448496 A | 5/2012 |
| CN | 103736093 A | 4/2014 |
| CN | 103784462 A | 5/2014 |
| WO | 2010/089046 A1 | 8/2010 |
| WO | 2011/049958 A2 | 3/2011 |
| WO | 2012/094283 A2 | 7/2012 |
| WO | 2017/074965 A1 | 5/2017 |
| WO | 2017/129457 A1 | 8/2017 |

OTHER PUBLICATIONS

Chaaban et al, "Cystic fibrosis chronic rhinosinusitis: A comprehensive review", American Journal of Rhinology & Allergy (2013), vol. 27, pp. 387-395, DOI: 10.2500/ajra.2013.27.3919.

Shikani et a., "Topical Gel Therapy for Sinonasal Polyposis in Samter's Triad: Preliminary Report ", Annals of Otology, Rhinology & Laryngology (2012), vol. 121, No. 11, pp. 719-724, DOI: 10.1177/000348941212101104.

Pandey et al, "Formulation, functional evaluation and ex vivo performance of thermoresponsive soluble gels—A platform for therapeutic delivery to mucosal sinus tissue", European Journal of Pharmaceutical Sciences (2017), vol. 96, pp. 499-507, Published Online Oct. 19, 2016, DOI: 10.1016/j.ejps.2016.10.017.

* cited by examiner

IN SITU GEL-FORMING PHARMACEUTICAL COMPOSITIONS AND USES THEREOF FOR SINUS DISEASES

CROSS-REFERENCE TO RELATED APPLICATION

This application is the US national phase of International Application No. PCT/US2018/049333, filed on Sep. 4, 2018, which claims priority to U.S. Application No. 62/553,806, filed on Sep. 2, 2017, the contents of both of which are incorporated herein by reference in their entirety.

BACKGROUND OF THE INVENTION

Chronic rhinosinusitis (CRS) is often the result of mixed inflammatory and infectious processes that concurrently affect the nose and para-nasal sinuses. It is a debilitating disease that can lead to significant physical symptoms and substantial functional impairment. The condition is defined by a constellation of symptoms and prolonged clinical course, affecting as many as 30 million US adults per year. See, e.g., Pearlman et al., "Review of current guidelines related to the diagnosis and treatment of rhinosinusitis," Curr Opin Otolaryngol Head Neck Surg (June 2008), 16 (3): 226-30. Persistent infection can lead to chronic mucosal inflammation, altered sinonasal ciliary function, and nasal polyp formation. The treatment of multiple drug-resistant rhinosinusitis remains largely ineffective. See, e.g., Chiu at al., "An animal model for the study of topical medications in sinusitis," Am. J. Rhinol. 2007, 21 (1), 1-9. The established role of bacterial biofilms in chronic diseases, such as CRS, and their formidable resistance to conventional medical and surgical therapies poses a significant problem to the treating physician. See, e.g., Ramadan et al., "Chronic rhinosinusitis and biofilms," Otplaryngol Head Neck Surg., 2004, 132:414-417.

A particularly difficult sub-set of CRS patients also suffer from cystic fibrosis (CF). This inherited disease, caused by abnormalities of a specific gene called CFTR, affects a small (approx. 30,000) number of, but extremely sick, children in the US. Because CF impairs the body's ability to fight and clear infections, kids with CF get sicker and stay sicker longer. Chronic sinusitis in CF can cause multiple symptoms including fever, runny nose, facial pain, headaches, nasal airway blockage and congestion due to the inflammatory changes of the sinonasal mucus membrane. Since there is no cure for cystic fibrosis, an effort should be made to maintain the functionality of the upper airway and to minimize symptoms of reactive airway exacerbation due to recurrent infections. Recent studies have shown that there is significant correlation between the organisms cultured from the paranasal sinuses and bronchoalveolar lavage of patients with cystic fibrosis. Two major species of the organisms appear to be pseudomonas and staphylococcus. Furthermore, it is believed that these two organisms form chronic, recalcitrant biofilm infections within the sinonasal cavity and become the reservoir for sustained recurrent pulmonary infections. Many children with cystic fibrosis eventually require repeated sinus surgery followed by lung transplant. Eliminating both planktonic and biofilm infections in these chronically ill pediatric cases may be a way to prevent repeated sinus surgery while increasing the safety and longevity of transplanted lungs.

The treatment of patients with cystic fibrosis includes eradicating the reservoir of microbial biofilm, reducing the inflammatory changes of the sinonasal cavity and eliminating recurrent sinus infections. Almost all children with cystic fibrosis suffer from a lifetime of chronic infection, long-term antibiotics, poor respiratory function and chronic sinusitis. If the chronic sinusitis and the resultant bacterial seeding can be eliminated, the prognosis for these patients can be significantly improved.

A variety of approaches have been known for some time that can address different aspects of the disease process. For instance, irrigation and lavage can alleviate congestion, antibiotics and antifungals can remove inciting pathogens and anti-inflammatories can temper the inflammatory cascade. However, there are limitations associated with each of these currently known therapeutic approaches that render each inadequate when taken in isolation. Saline irrigation has been successful in many cases of CRS but suffers from limited antimicrobial potency and little or no effect in more seriously infected cases. Saline irrigation alone, including both hypertonic and hypotonic formulations, is not effective in the long-term reduction of pathogen colonization or the prevention of biofilm formation. Antibiotics and antifungals have been used with varying degrees of success in CRS, as intravenous (IV) infusions, oral agents and irrigation additives. Specific antibiotic therapy, in whatever form, is doomed to fail due to the chronic nature of the disease requiring prolonged therapy. These two factors contribute to the development of conventional bacterial resistance. They also create the physiologic conditions that promote the formation of biofilms, further limiting their ability to eradicate inciting organisms. Finally, steroids in general and the "nasal steroids" in particular are important tools for the control of the steroid-responsive inflammation that complicates chronic infection. While no single therapy is adequate to address all of these pathogenic factors, in many difficult cases even the best currently known combination therapies are ineffective.

Moreover, a significant challenge of nasal drug development is to overcome the protective barriers of the nasal cavity without causing permanent tissue damage. The major problems that persist with nasal solutions are cleared off rapidly from the nasal cavity. The half-life of clearance for both liquid and powder formulations that are not mucoadhesive is in the order of 15-20 minutes. See, e.g., Galgatte et al., "Development of in situ gel for nasal delivery: design, optimization, in vitro and in vivo evaluation," Drug Delivery 2014, 21(1): 62-73.

Accordingly, the inventors have conceived and validated a strategy to decrease the mucocilliary clearance by the use of mucoadhesive gel formulations to prolong the residence time at the nasal absorption site, thereby facilitating the uptake of the drug. Because human nasal mucosa is covered with approximately 0.1 mL mucus, which consists of sodium, potassium and calcium ions, a solution-gel phase transition will occur with ion-sensitive gel formulations.

Accordingly, the present invention provides in-situ gel-forming formulations containing an antiseptic (particularly povidone iodine) and corticosteroids by using polysaccharide gel matrix, where the effective concentrations of the antiseptic and corticosteroids (i.e., solution drug substances) are maintained by the equilibrium between the solution drug substances and the gel bound components. This therapeutic strategy has the potential to drastically decrease dependence on chronic oral antibiotics in cystic fibrosis patients, enable more successful pulmonary transplant prognosis and greatly improve the life quality of the patients.

Although a variety of agents have shown promise in anti-biofilm studies, none has yet been developed that combines the antibacterial, antifungal and anti-inflammatory properties that are likely needed to eradicate the causative agents and treat the concomitant inflammatory response that accompanies most chronic sinus infections. See, e.g., Liu Y. et al., "In Situ Gelling Gelrite/Alginate Formulations as Vehicles for Ophthalmic Drug Delivery," AAPS PharmSciTech, Vol. 11, No. 2, June 2010, 610-620. An approach to address this problem was previously presented by us that employed the common antiseptic povidone-iodine at a non-toxic dilution in combination with suspended budesonide in a nasal irrigation suspension. This formulation has already been used to successfully reduce symptom scores in a small series of refractory CRS patients. See, e.g., WO 2012/177251. An in vitro assay was also performed to further characterize the anti-biofilm effect of this clinically successful treatment against organisms known to form biofilms in human CRS infections. Supra. The optimization of in-situ gelling sustained-release formulations resulted in a long lasting, less toxic pharmacological effect, while reducing sedimentation of budesonide suspension with more uniform drug formulation for effective treatment of CRS in the meantime.

It's our goal to develop a treatment program to address the common features of CRS across the whole spectrum of the disease—infection by micro-organism (e.g., bacterial, fungal, biofilm, etc.), host inflammatory response leading to mucosal edema, and long acting resulting in better efficacy and patient compliance. The challenge remains to be finding a non-surgical agent that can (1) eliminate infections including biofilms, (2) reduce airway inflammation, and (3) be made into a long-lasting formulation resulting in less frequent dosing and reduced dosage with minimized toxicity.

It's surprisingly discovered that this therapeutic challenge can be addressed by combining antiseptics and anti-inflammatories with a sustained release in-situ gel-forming drug delivery technology. This strategy addresses the underlying infectious pathology from both planktonic and biofilm sources, and can alleviate the concomitant inflammatory response, with a longer therapeutic effect. This tripartite approach to chronic sinus disease addresses all causative pathways and chemically reduces the host immune response that leads to prolonged disease.

BRIEF SUMMARY OF THE INVENTION

This invention provides aqueous pharmaceutical compositions each comprising an antiseptic, a steroid, and a biocompatible polysaccharide, wherein the composition can form a gel in situ upon instillation into a sinonasal cavity of a subject in need thereof for treating a sinus symptom of the subject.

In some embodiments, the antiseptic comprises an iodine-containing compound. Such an iodine-containing compound can be an iodophor which includes iodine complexed with a solubilizing agent. Examples of suitable solubilizing agents comprise organic polymers, alcohols, polyols, surfactants, surface active anions, cations, or detergents. One example of the iodine-containing compound is povidone-iodine complex (PVP-I).

In some embodiments, the concentration of the povidone-iodine complex (PVP-I) in a fully constituted aqueous solution of the pharmaceutical composition of this invention (which means that the solution is ready for the intended uses of this invention, e.g., by irrigating or spraying into a patient's nasal cavity) ranges from 0.01% to 10% by weight/weight or weight/volume, from 0.1% to 2.5% by weight/weight or weight/volume, from 0.15% to 1.5% by weight/weight or weight/volume, from 0.2% to 1.0% by weight/weight or weight/volume, or 0.2% by weight/weight or weight/volume.

In an embodiment, the PVP-I concentration in the aqueous pharmaceutical composition of this invention is measured on a weight/weight basis with respect to the overall solid weight of the packaged preparation. In another embodiment, the PVP-I concentration in the pharmaceutical composition of this invention is measured on a weight/volume basis with respect to the overall preparation when combined with water.

In some embodiments, a suitable steroid in the aqueous pharmaceutical composition of this invention comprises mometasone, fluticasone, or budesonide, or a salt, an ester, or any combination thereof.

In some embodiments, the polysaccharide in the aqueous pharmaceutical composition of this invention comprises deacetylated gellan gum (DGG), xanthan, sodium alginate, carrageenan, or any mixture thereof. The polysaccharide may be contained in the pharmaceutical composition of this invention at a concentration in the range of 0.1% to 2.0% (weight/weight or weight/volume), or 0.1% to 0.5% (weight/weight or weight/volume).

In one embodiment, the polysaccharide is deacetylated gellan gum (DGG). Deacetylated gellan gum (an exocellular polysaccharide of microbial origin, commercially available as Gelrite®) is an interesting in-situ gelling polymer that seems to perform very well in humans. Rozier et al., "Gelrite®: a novel, ion-activated, in situ-gelling polymer for ophthalmic vehicles effect on bioavailability of timolol," Int J Pharm., 1989; 57:163-8; Liu et al., "In Situ Gelling Gelrite/Alginate Formulations as Vehicles for Ophthalmic Drug Delivery," AAPS PharmSciTech, Vol. 11, No. 2, June 2010, 610-620; and Agnihotri et al., "Controlled release of cephalexin through gellan gum beads: effect of formulation parameters on entrapment efficiency, size, and drug release," Eur J Pharm Biopharm. 2006; 63:249-61. Deacetylated Gellan Gum (Gelrite®) is an anionic linear polysaccharide comprised of a plurality of four-sugar units. Because human nasal mucosa is covered with approximately 0.1 mL mucus which includes sodium, potassium and calcium ions, a solution-gel phase transition can be expected with ion-sensitive gel formulations.

In some other embodiments, the aqueous pharmaceutical composition of this invention may further include an osmotic pressure regulator, a surfactant, a viscosity increasing agent, a pH regulator, or a cooling agent. Examples of suitable osmotic pressure regulator include sodium chloride, glycerol, polyethylene glycol 400 (PEG400), mannitol, and boric acid. The osmotic pressure regulator may be contained in the aqueous pharmaceutical composition at a concentration in the range of 0.1% to 0.5% (w/w or w/v). Examples of a suitable surfactant include polysorbate-20, polysorbate-60, polysorbate-80, polyoxyethylene surfactant, polyoxypropylene surfactant, glycerin, cyclodextrin, tyloxapol, PEG 35 Caster oil, polyoxyl 40 Strerate, and any combination thereof. The surfactant in the aqueous pharmaceutical composition can have a concentration ranging from 0.01% to 2% by weight. Examples of a suitable viscosity increasing agent include polyvinyl alcohol, polyvinylpyrrolidone, methyl cellulose, hydroxypropylmethylcellulose, hydroxyethylcellulose, carboxymethylcellulose, hydroxypropylcellulose, microcrystalline cellulose, carboxymethyl cellulose sodium, dextrose anhydrous, and any of their combinations. The concentration of the viscosity agent can range from 0.01% to 2% by weight. Examples of a suitable bioadhesive agent include polyvinylpyrrolidone, xanthan gum, locust bean gum, acacia gum, hydroxypropyl methylcellulose, sodium alginate, pectin, gelatin, carbomer, polyvinylalcohol, gellan gum, tragacanth, acacia, sodium carboxymethyl cellulose, or any of their combinations. Examples of a suitable cooling agent include menthol, methane glycerin acetyl, menthyl ester, carboxamide, menthane glycerol ketal, alkyl substituted urea, sulfonamide, terpene analogs franone, phosphine oxide, derivative thereof, camphor, bonel, and any of their combination.

In some other embodiments, the pharmaceutical compositions can be in the form of a solution (e.g., an aqueous solution), a suspension, an emulsion, a dry sterile powder, a controlled-release vehicle, or a sustained-release vehicle. They can be administered directly, or diluted or constituted with purified water or an aqueous saline, when needed and in situ, to give a low iodine concentration and subsequently administered to a patient in need thereof, e.g., by washing or irrigation of the patient's sinal cavity or by spraying into it.

Though iodine is well known to readily react with steroids, the aqueous pharmaceutical compositions of this invention are surprisingly and unexpectedly stable, as the steroid contained therein (e.g., mometasone, fluticasone, budesonide, or a salt or adduct thereof) has been able to resist iodination, iodine oxidation and iodine-catalyzed addition reactions whether in solution, suspension or in the dry-powder state. Examples of iodine compounds suitable for the compositions of this include iodophors (e.g., complexed with povidone, organic polymers, alcohols, polyols, surfactants, surface active anions and cations, detergents, or others known in the art). See, e.g., U.S. Pat. Nos. 2,706,701; 2,826,532; 3,039,916; 2,860,080; 2,840,510; and 2,759,869.

Such surprisingly stable pharmaceutical compositions containing highly toxic iodine and anti-inflammatory steroids are capable of synergistically treating sinus symptoms and inhibiting or even eliminating biofilms without casing toxic inflammatory reactions of the sin-nasal tissues. Additionally, these compositions are able to limit the inflammatory cascade and eliminate microbial activators of inflammation because of their ability to safely deliver antiseptic iodine and minimally absorbed sinonasal steroids.

Iodine and steroid have both been used in treating nasal conditions or diseases. Most iodine preparations are toxic at useful concentrations, with the exception of iodophoric agents like povidone-iodine. Budesonide is the identical active ingredient present in the approved inhaled steroid preparation Pulmicort which is a widely used, safe and effective intervention employed by sinus disease specialists as an agent for suspension irrigation into the sinuses. See, e.g., Bhalla et al., "Safety of budesonide in saline sinonasal irrigations in the management of chronic rhinosinusitis with polyposis: lack of significant adrenal suppression," J. Otolaryngol Head Neck Surg. 2008; 37(6): 821-5.

Povidone-iodine is a widely used pre-surgical antiseptic known to be safe and effective in a variety of formulations for the prophylaxis and treatment of mucosal and skin surface infection. There have been countless clinical studies demonstrating the safety of PVP-I in a variety of topical applications in ophthalmology, otology, rhinology and dermatology. See, e.g., Bhagwat et. al., U.S. Pat. No. 5,126,127; Liang et. al., US 2007/0219170; Jaya et al., "Evaluation of topical povidone-iodine in chronic suppurative otitis media," Arch Otolaryngol Head Neck Surg," 2003 October; 129 (10):1098-100; Rooijackers-Lemmens et al., "NHG-standard otitis externa," Huisarts Wet 1995; 28(6):265-71; Rowlands et al., "Otitis externa in UK general practice: a survey using the UK General Practice Research Database," Br J Gen Pract 2001; 51:533-8; and Perez et al., "Vestibular and cochlear ototoxicity of topical antiseptics assessed by evoked potentials," Laryngoscope, 2000 (110): 1522-1527.

By employing a non-toxic, highly biocidal antiseptic with a powerful nasal steroid, we have been able to control both infectious and inflammatory aspects of chronic rhinosinusitis (CRS). We have shown in our proprietary suspension formulation that we can eliminate established biofilms of both *Staphylococcus aureus* and *Pseudomonas aeruginosa* and established biofilms of fungus (*C. albicans*).

Most significantly, we have shown that povidone iodine/budesonide suspensions can be safely employed in sinusitis occurring in patients secondary to cystic fibrosis and patients treated via sinonasal irrigation with a dilute PVP-I/budesonide suspension have subjective and objective evidence of improvement. See Liang et al., WO 2012/177251. A combination of dilute povidone-iodine and budesonide has been employed in Connecticut Sinus Institute for the treatment of chronic recalcitrant rhinosinusitis through sinonasal irrigation. A retrospective review of clinical experience with this regimen was undertaken to evaluate the tolerability and efficacy of this therapy. A total of five patients were identified and included in this retrospective study. None discontinued use due to intolerance. There were no reported adverse advents. The mean post-treatment improvement in the subjective symptoms as measured by scaled scores on a validated sinonasal outcomes test was 31. Pre-treatment cultures were positive for 5/5 patients with multi-resistant species including MRSA, *Enterococcus, Acenitobacter, Pseudomonas, Propionobacterium, S. viridans, Klebsiella* and *Serratia*. Post-treatment cultures were positive 2/5 patients only for *S. aureus, Pseudomonas* and *Enterococcus*.

By employing both a well-described nasal steroid and a potent, non-toxic poly-antimicrobial through our proprietary sustain release in-situ gel forming technology, we have achieved a long acting effect on improvement of both symptom scores [measured by verified assessment vehicle Sino-Nasal Outcome Test-22 [SNOT-22] questionnaire (Piccirillo et al., Psychometric and clinimetric validity of the 20-item Sinonasal Outcome Test (SNOT-20), Otolaryngol Head Neck Surg., 202, 126:41-47)] and bacteriologic parameters (assessed by pre- and post-treatment culture) in patients suffering from CRS.

With polysaccharide as the gel forming matrix, the aqueous pharmaceutical compositions of this invention have shown unexpected and surprising ability to release, in a sustained manner, both povidone iodine and steroids in the dissolution models. It was also unexpectedly and surprisingly discovered that povidone iodine and polysaccharides can form an in-situ gel forming matrix, which significantly increases steroids' stability in the pharmaceutical compositions without sedimentation after storage over a long period time.

It was also surprisingly discovered that steroids have unexpectedly increased solubility in the aqueous pharmaceutical compositions of this invention, which potentially increase bioavailability of steroids in patients.

Optimizing the in-situ gel forming compositions of this invention, which contained povidone iodine and steroids, resulted in unexpectedly stable formulation systems with in-situ gel forming characteristics under simulated physiological nasal conditions through both thermo-sensitive and ion-sensitive sol-to-gel transition mechanisms.

Moreover, the aqueous formulations of this invention may be made more effective by the addition of a dilute topical anesthetic, e.g., for elimination of pain associated with the drop and enhanced penetration of anti-infective compounds into ocular structures. Accordingly, the aqueous formulations of this invention are also effective in the prevention of infection and/or inflammation in the post-operative patients.

As used herein, the term "aqueous pharmaceutical composition" means that the composition mainly (e.g., at least 75%, at least 80%, at least 90%, at least 95%, or at least 99%, volume by volume) contains water as the medium but may or may not include other pharmaceutically acceptable solvent such as ethanol, and the composition is intended for inducing therapeutic effects by reducing or eliminating clinical symptoms of a disease.

As used herein, the term "subject" means a mammal and includes human and non-human.

As used herein, the term "gel" refers to a semi-solid or solid jelly-like material that can have properties ranging from soft and weak to hard and tough and exhibits no flow when in the steady-state.

As used herein, the term "antiseptic" refers to a therapeutic agent that has the effect to eliminate or reduce the infectious symptoms.

As used herein, the term "polysaccharide" refers to a polymeric carbohydrate molecule composed of long chains of monosaccharide units bound together by glycosidic linkages and on hydrolysis give the constituent monosaccharides or oligosaccharides. They can be natural or synthetic, and they range in structure from linear to highly branched. Examples include storage polysaccharides such as starch and glycogen, and structural polysaccharides such as cellulose and chitin.

As used herein, the term "biocompatible" refers to the ability of a material to perform with an appropriate host response in a specific situation such as temperature or ion strength.

As used herein, the word "a" or "an" can be interpreted to introduce a plural form of a noun, unless such interpretation results in contrary or inoperative meaning. Additionally, the word "a" or "an" can be interpreted to mean "any."

As used herein, the work "or" shall also mean "and" unless such interpretation results in contrary or inoperative meaning.

BRIEF DESCRIPTIONS OF THE DRAWINGS

Figure 2:
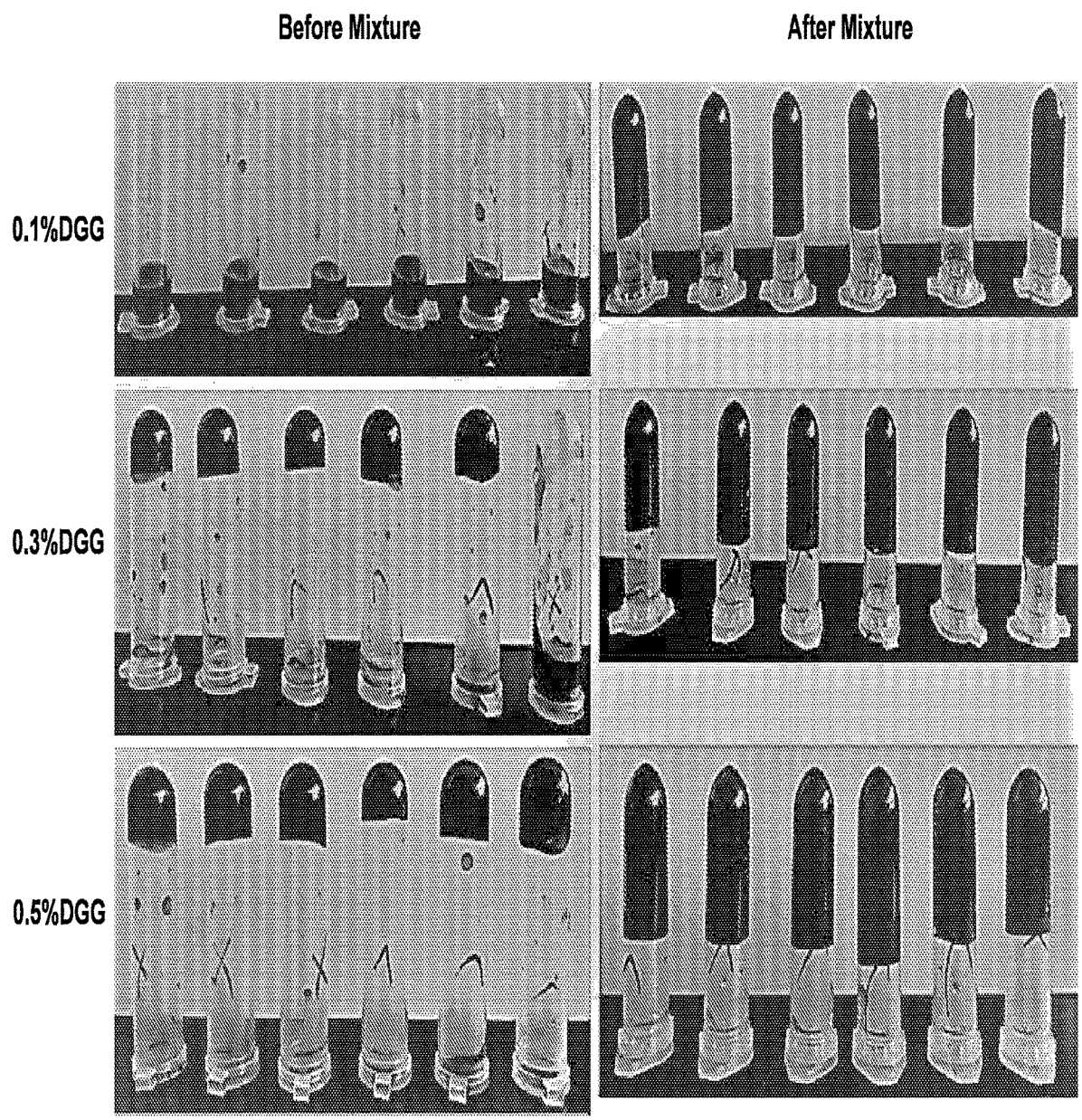
Figure 3:
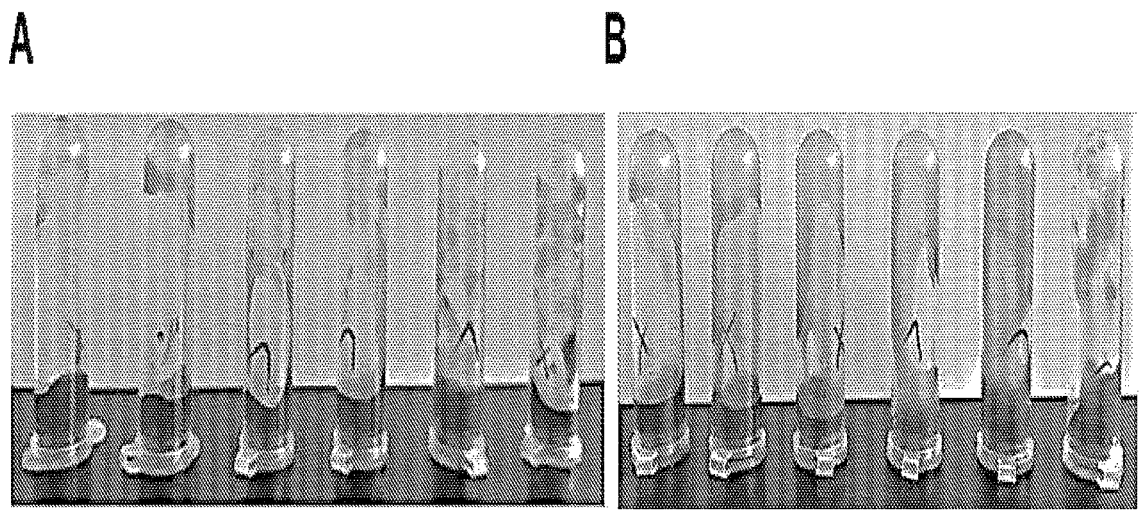
Figure 4:
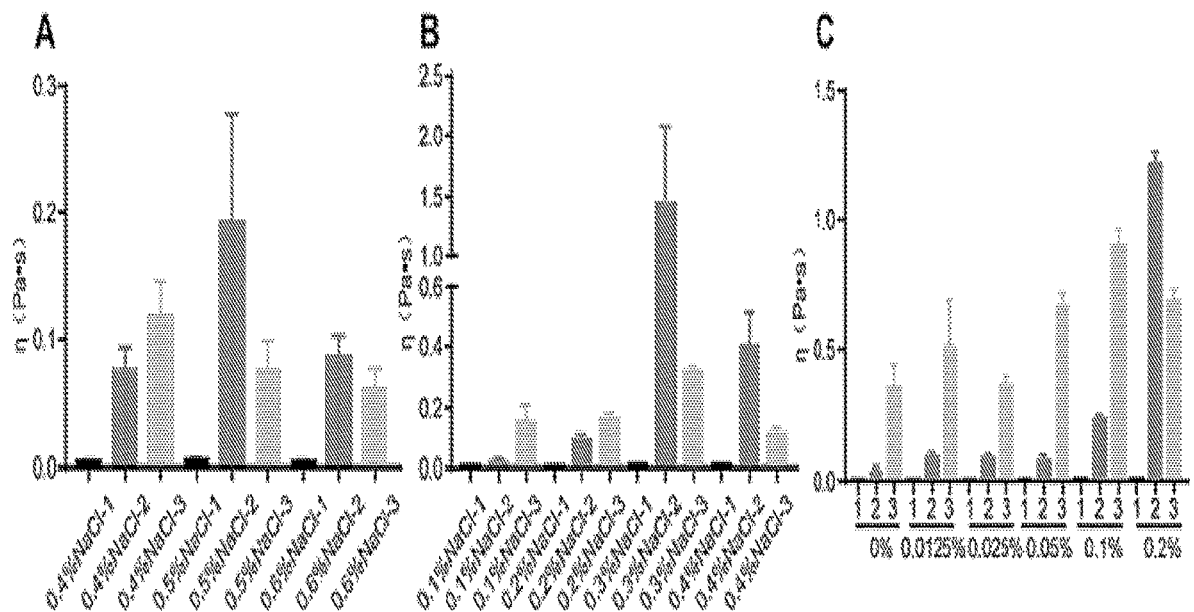
Figure 5:
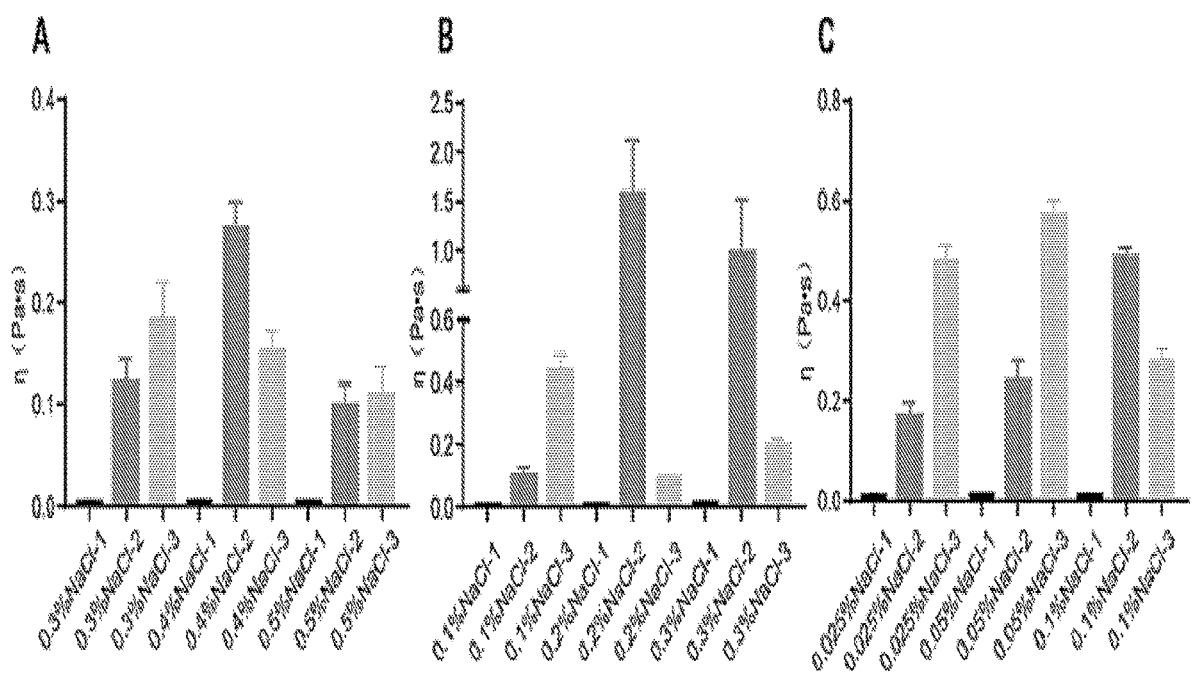
Figure 6:
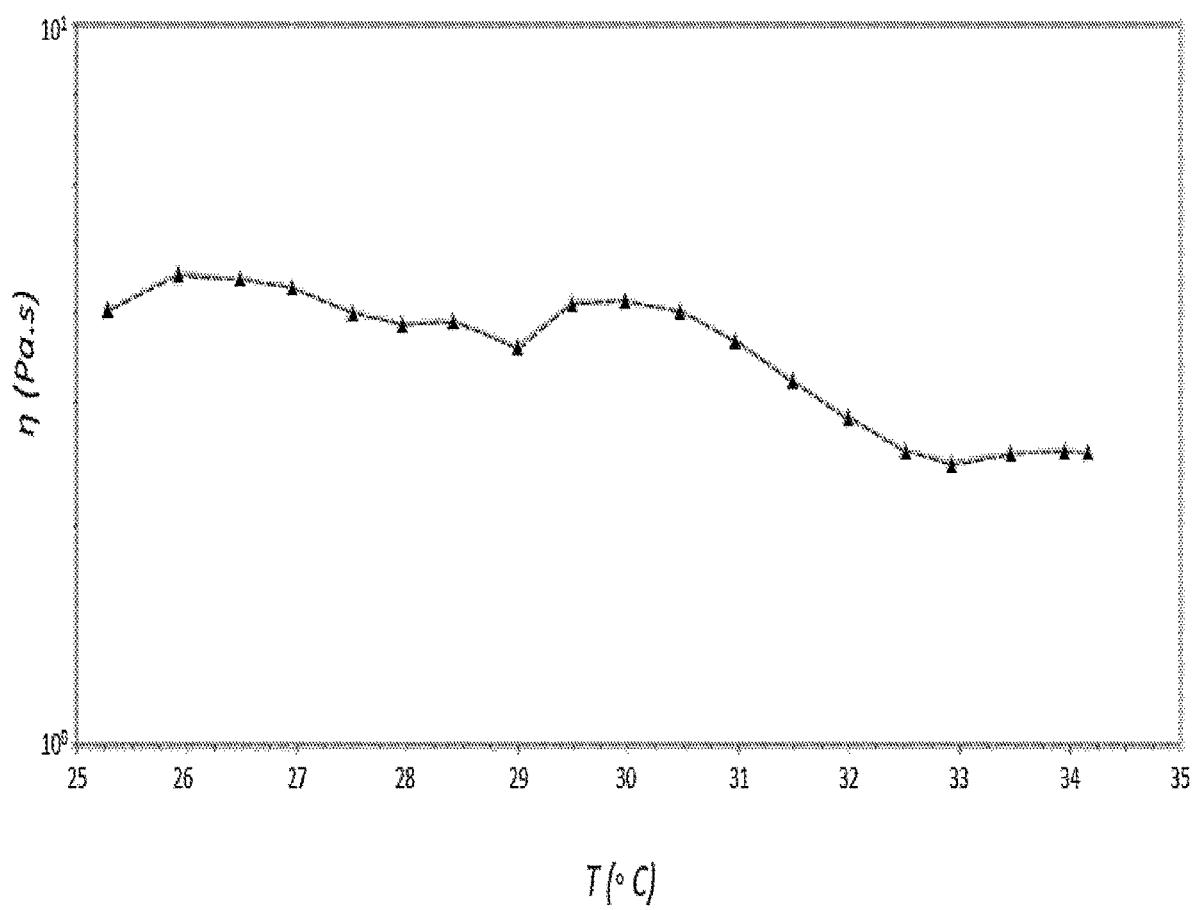
Figure 7:
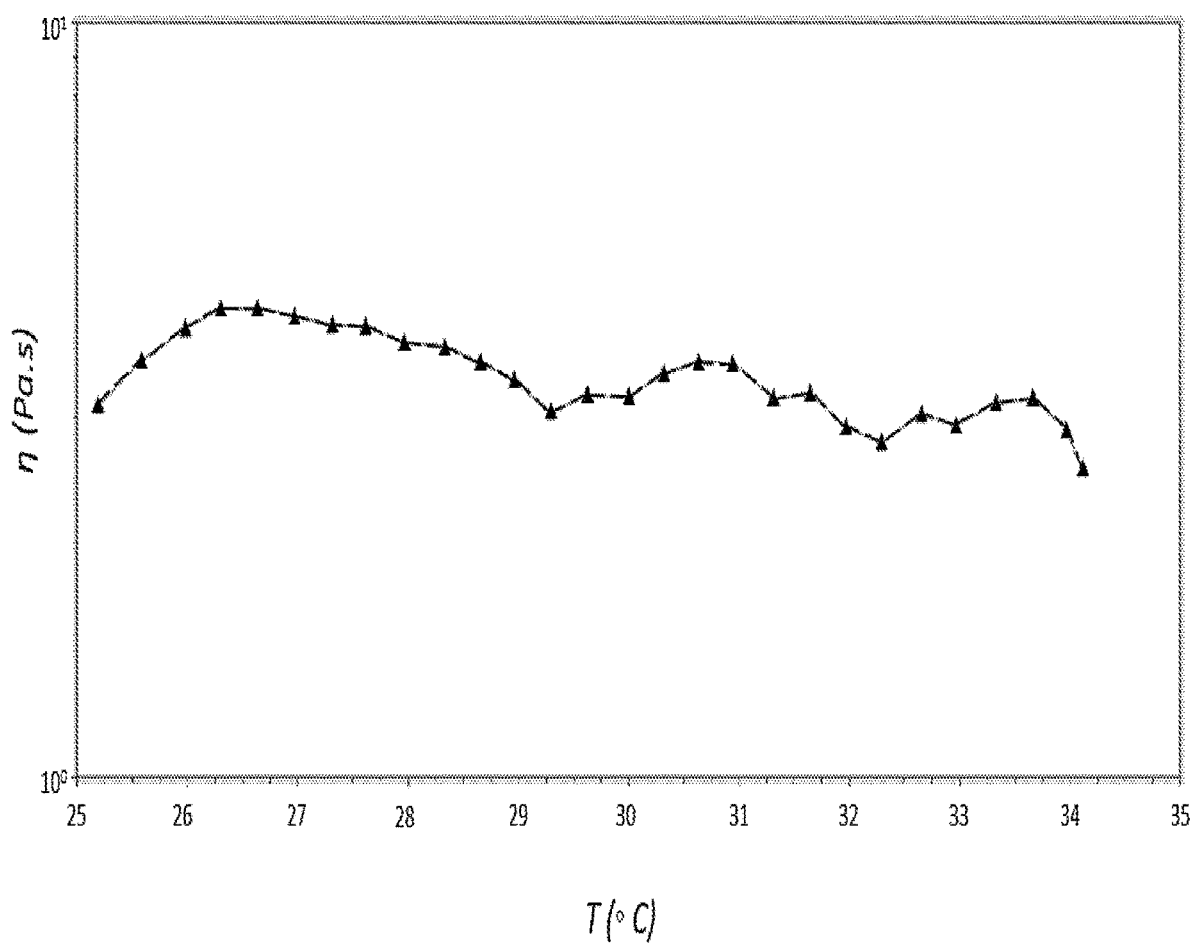
Figure 8:
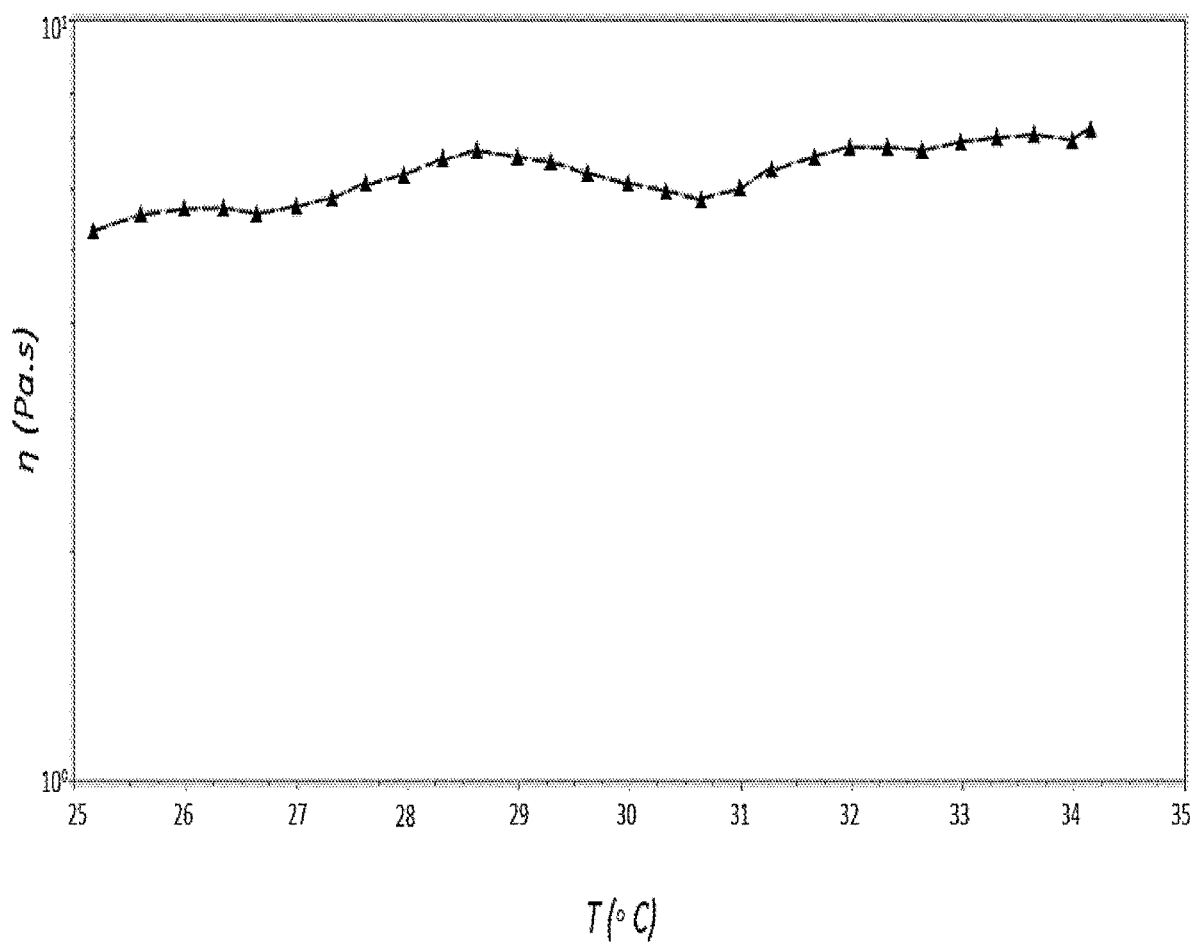
Figure 9:
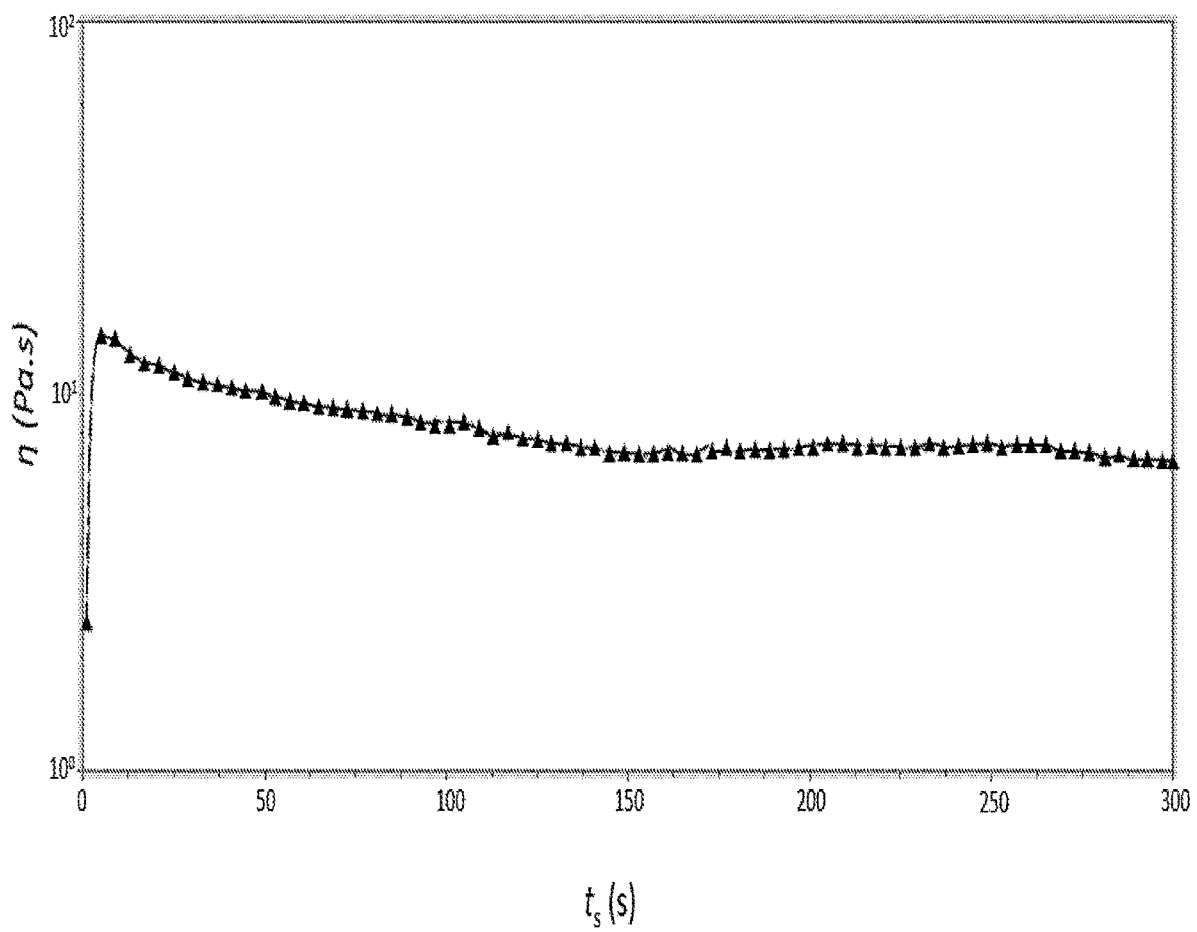
Figure 10:
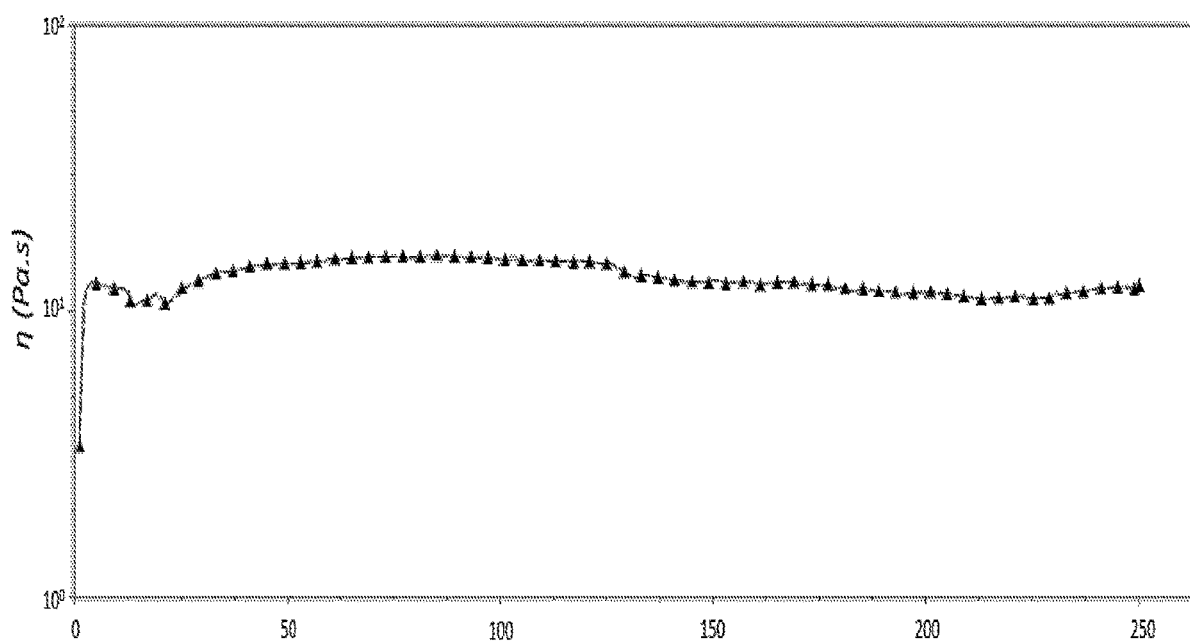
Figure 11:
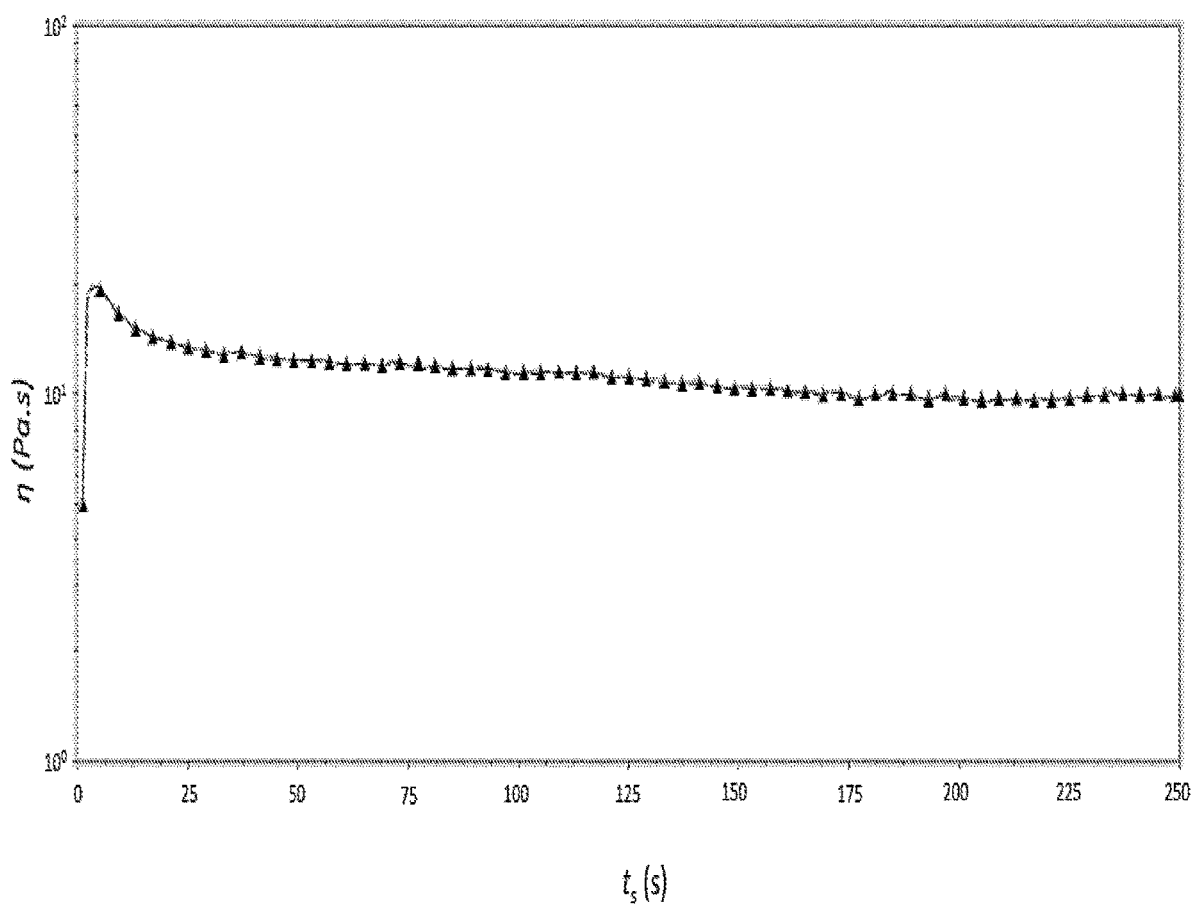
Figure 12:
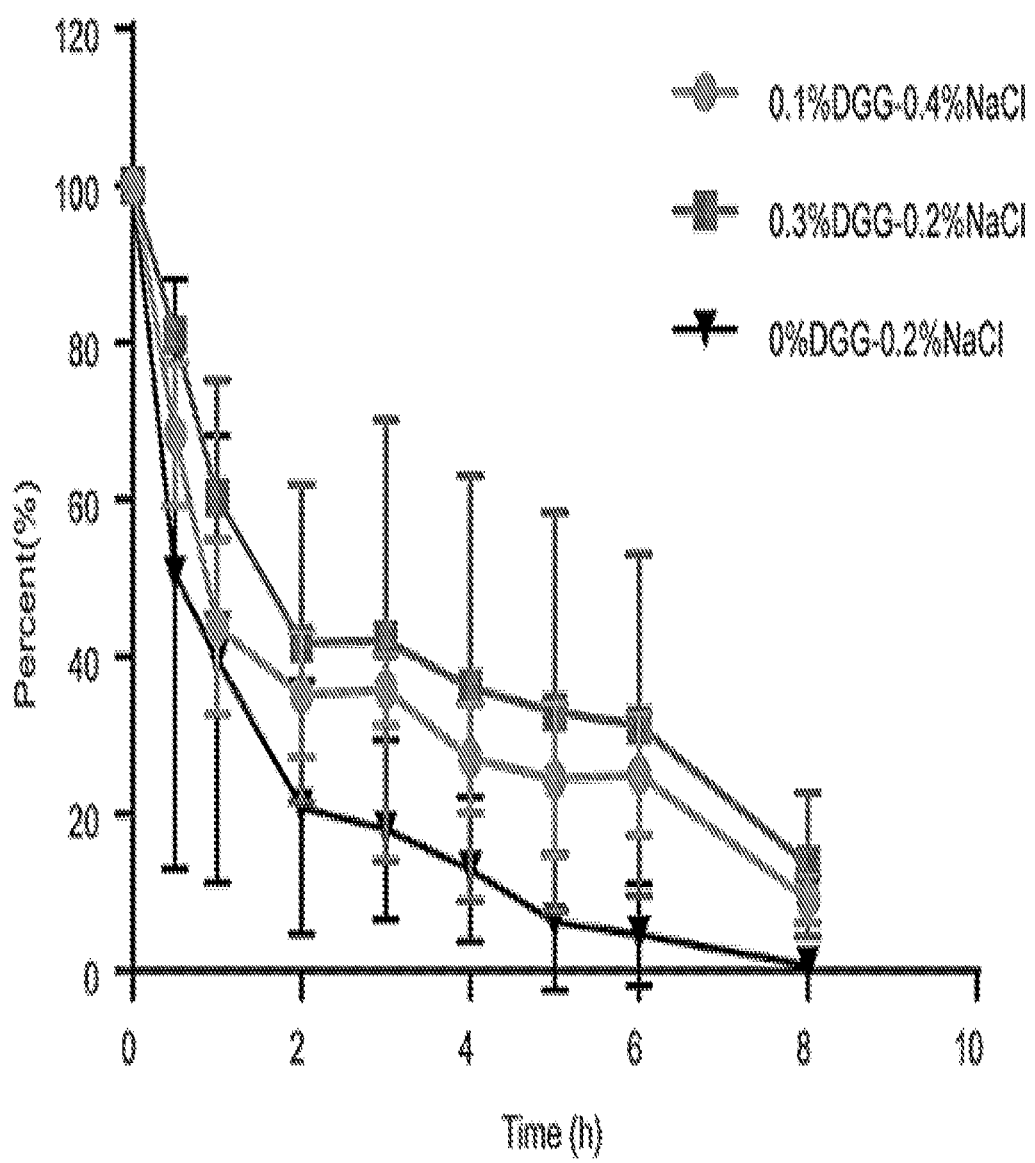
Figure 13:
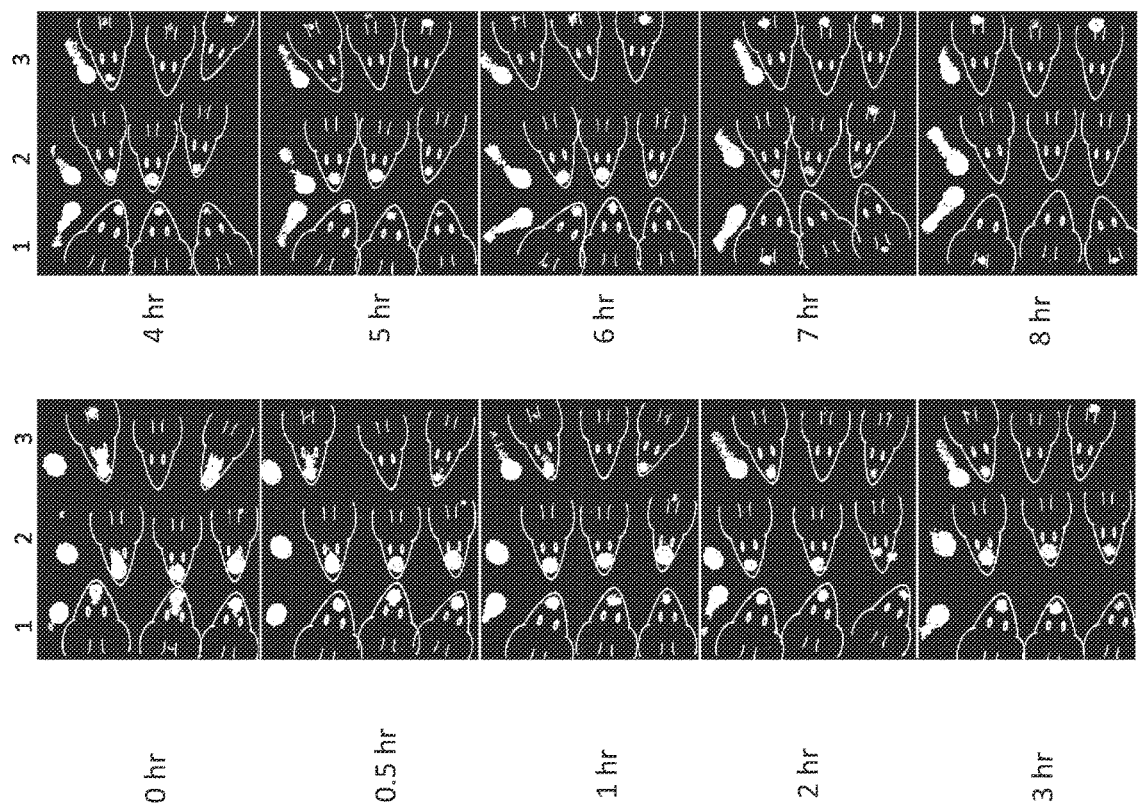
Figure 14:
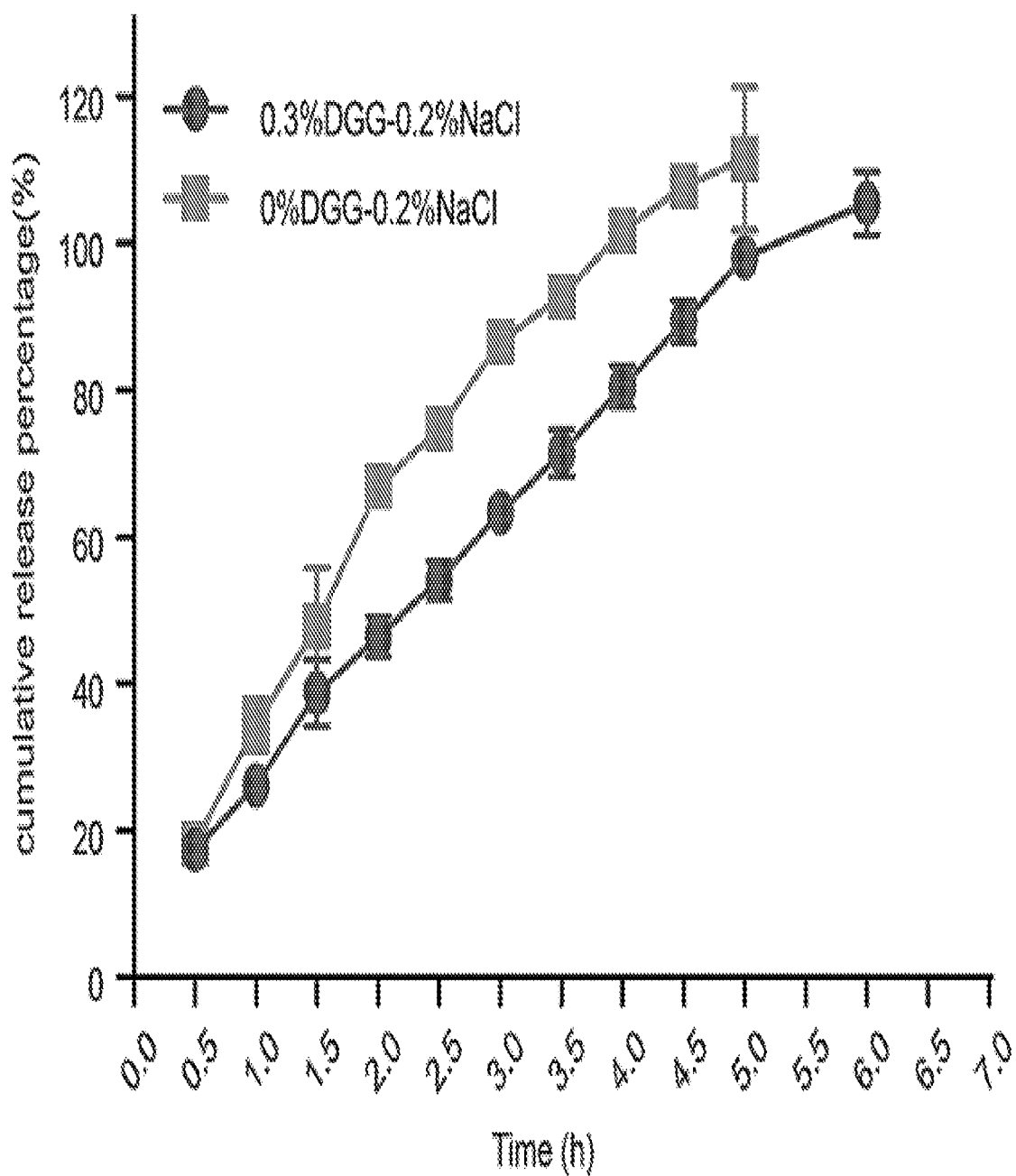

FIG. 1 shows the viscosity of different compositions.
FIG. 2 shows gel-forming condition of different compositions.
FIG. 3 shows the physical states of compositions containing 0.8% PVP-I.
FIG. 4 shows the viscosity of compositions containing 0.5% PVP-I with different NaCl concentrations.
FIG. 5 shows the viscosity of compositions containing 0.8% PVP-I with different NaCl concentrations.
FIG. 6 shows the viscosity of composition 1 over a period of time, before mixing with 0.1% NaCl.
FIG. 7 shows the viscosity of composition 2, over a period of time, before mixing with 0.15% NaCl.
FIG. 8 shows the viscosity of composition 3 over a period of time, before mixing with 0.2% NaCl.
FIG. 9 shows the viscosity of composition 1 over a period of time, after mixing with 0.1% NaCl.
FIG. 10 shows the viscosity of composition 2, over a period of time, after mixing with 0.15% NaCl.
FIG. 11 shows the viscosity of composition 3 over a period of time, after mixing with 0.2% NaCl.
FIG. 12 shows nasal cavity residual rate distribution-time curves of different compositions.
FIG. 13 shows different gamma camera distribution results.
FIG. 14 shows accumulated release curves.

DETAILED DESCRIPTION OF THE INVENTION

This invention provides an aqueous pharmaceutical composition comprising an antiseptic, a steroid, and a biocompatible (and environmentally sensitive) polysaccharide, for treating a sinus symptom of a patient, wherein the composition forms (or transform into) a gel in situ upon instillation into the sinonasal cavity of a subject.

The antiseptic contained in the compositions of this invention may be PVP-I or chlorhexidine. The concentration of the antiseptic (e.g., PVP-I or chlorhexidine) may range from 0.1% to 5% (w/w or w/v), from 0.3% to 1% (w/w or w/v), or from 0.2% to 0.6% (w/w or w/v). An example of chlorhexidine suitable for this invention is chlorhexidine digluconate, with its concentration in the compositions ranging from 0.02% to 2% (w/w or w/v), from 0.02% to 0.5% (w/w or w/v), or from 0.02% to 0.2% (w/w or w/v).

The steroid contained in the compositions of this invention may include mometasone, fluticasone, or budesonide, or a salt, an ester, or any combination thereof. Example of a suitable steroid for the compositions of this invention include micronized mometasone, micronized fluticasone, or micronized budesonide, with its concentration in the compositions ranging from 0.02% to 0.1% (w/w or w/v).

The polysaccharide contained in the compositions of this invention may include deacetylated gellan gum (DGG), xanthan, sodium alginate and carrageenan, or any mixture thereof. Deacetylated gellan gum may be preferred, with a concentration ranging from 0.1% to 1% (w/w)—e.g., from 0.3% to 0.5% (w/w)—in the compositions.

The aqueous pharmaceutical compositions of this invention may additionally include an osmotic pressure regulator, a surfactant, a viscosity increasing agent, a pH regulator, a cooling agent, or a combination thereof.

The osmotic pressure regulator contained in the compositions of this invention may include sodium chloride, glycerol, polyethylene glycol 400 (PEG400), mannitol, or borate, with a concentration ranging from 0.1 to 0.9% (w/v) or from 0.2 to 0.4% (w/v).

Examples of a surfactant suitable for the compositions of this invention include polysorbate-20, polysorbate-60, polysorbate-80, polyoxyethylene surfactant, polyxoypropylene surfactant, glycerin, cyclodextrin, tyloxapol, PEG 35 Caster oil, polyoxyl 40 Strerate, or any combination thereof. The surfactant in the pharmaceutical compositions can have a concentration ranging from 0.01% to 2% by weight.

Examples of a viscosity-increasing agent suitable for this invention include polyvinyl alcohol, polyvinylpyrrolidone, methyl cellulose, hydroxypropylmethylcellulose, hydroxyethylcellulose, carboxymethylcellulose, hydroxypropylcellulose, microcrystalline cellulose, carboxymethyl cellulose sodium, dextrose anhydrous, or any of their combinations. The concentration of the viscosity-increasing agent in the compositions can range from 0.01% to 2% by weight.

Examples of a suitable pH regulator contained in the compositions of this invention include sodium hydroxide, trishydroxymethylaminomethane (Tris), hydrochloride (HCl), or phosphoric acid, resulting in a pH in the range of 4.0-7.0, or in the range of 4.0-6.0.

Another aspect of this invention provides a method for treating a clinical symptom of the airway of a subject (a patient), comprising administering to a sinal cavity of the patient in need therefore an aqueous pharmaceutical composition of this invention which contains an antiseptic compound, a steroid, and a biocompatible polysaccharide and which can form a gel in situ upon instillation into a sinonasal cavity of the subject.

In some embodiments, the sinus symptom is inflammation, infection, formation of biofilm, rhinosinusitis, congestion, pain, pressure, fatigue, or thickened nasal discharge.

In some other embodiments, the airway is sinus, nose, or lung.

In still some other embodiments, the pharmaceutical compositions of this invention are administered to the subject by a rinsing bottle, metered-dose, manual-pump spray, a metering, or an atomizing spray pump.

In still another aspect, the present invention provides a method for improving the lung condition of a cystic fibrosis patient, which includes washing the sinal cavity of the patient with an aqueous pharmaceutical composition of this invention which contains an antiseptic compound, a steroid, and a biocompatible polysaccharide and which can form a gel in situ upon instillation into a sinonasal cavity of the subject.

In some embodiments, the dose volume of the pharmaceutical composition administered to the patient is between about 10 mcg to about 300 mcg per day, about 20 mcg to about 200 mcg per day, about 30 mcg to about 100 mcg per day, or about 50 mcg per spray with two spray per nostril per day.

The invention is further elucidated with specific examples. It is understood that these examples are only used to describe the invention but not to intend to limit the scope of invention. The experimental methods with no specific conditions in the following examples, are usually prepared under conventional conditions in the literature or according to the conditions suggested by the excipient manufacturer. Unless specifically stated, all percentages, ratios, proportions or fractions in this invention are calculated by weight by weight. Unless specifically defined in this invention, all professional and scientific terms used herein have the same meaning as well-trained personnel may be familiar with. In addition, any methods and materials similar or equivalent to those recorded in this invention can be applied to this invention. The preferred embodiments and materials described herein are used only for exemplary purposes.

EXAMPLES

The compositions of this invention containing povidone iodine and budesonide are formulated with one or more ion-sensitive in-situ gel forming materials such as polysaccharides which allow increased residence time of the compositions in the nasal cavity. The compositions are optimized with povidone iodine and budesonide by investigating their viscosity vs. the concentrations of the gel matrix at 25° C., before and after addition of simulated nasal fluid (SNF), and under physiological conditions after addition of simulated nasal fluid (34° C.-SNF). A gel-forming matrix needs to have a higher viscosity after addition of SNF at 34° C. than its viscosity at 25° C. before addition of SNF. Only such a gel matrix can potentially form an in-situ gel.

Examples 1

Screening Suitable PVP-I Concentrations in the Formulation 0.064% (w/w) budesonide and 0.25% (w/w) NaCl were into compositions, gellan gum concentration was at 0.1%, 0.3%, 0.5% (w/w) separately, PVP-I concentration was set at 0.2%, 0.5%, 0.8%, 1.0% (w/w) separately. Different concentrations of gellan gum and PVP-I were mixed separately to investigate the basic properties of the compositions of this invention.

TABLE 1

| | Composition Details | | | | | |
|---|---|---|---|---|---|---|
| | Budesonid (w/w) | NaCl (w/w) | Glycerin (w/w) | Gellan Gum (w/w) | PVP-I (w/w) | Tromethamine |
| Composition 1 | 0.064% | 0.25% | 2.3% | 0.1% | 0.2% 0.5% 0.8% 1.0% | pH adjusted to 4-5.5 |
| Composition 2 | 0.064% | 0.25% | 2.3% | 0.3% | 0.2% 0.5% 0.8% 1.0% | |
| Composition 3 | 0.064% | 0.25% | 2.3% | 0.5% | 0.2% 0.5% 0.8% 1.0% | |

The sample viscosity was investigated before and after mixing with the simulating nasal fluid (SNF) at a high shear rate (100/s) at 25° C. and a low shear rate (0.1/s) at 34° C. This was to simulate the change of viscosity before and after the sample is sprayed into the nasal cavity and the drug contacts the nasal simulating fluid, and to compare the sample's ability to spray and the gel forming ability when mixing with the nasal simulating fluid. The difference between the sample viscosity of the low shear rate (0.1/s) at 34° C. after mixing with SNF and the sample viscosity of the high shear rate (100/s) at 25° C. was labelled as $\Delta\eta 1$ (Pa·s); the difference between the sample viscosity of the low shear rate (0.1/s) at 34° C. after mixing with SNF and the sample viscosity of the low shear rate (0.1/s) at 34° C. as was labeled as $\Delta\eta 2$ (Pa·s).

TABLE 2

| Sample Viscosity Determination Conditions | | | |
|---|---|---|---|
| | Condition 1 (Before Mixing) | Condition 2 (Before Mixing) | Condition 3 (After Mixing) |
| Plate Diameter (mm) | 20 | 20 | 20 |
| Speed (s) | 100 | 0.1 | 0.1 |
| Temperature (° C.) | 25 | 34 | 34 |

Experiment results are shown in Tables 3 and 4, and FIG. 1 is drawn based on the data in Table 3. Specifically, FIG. 1 shows the viscosity of different compositions. In FIG. 1, A, B, C represent the viscosity of compositions with 0.1% DGG, 0.3% DGG, 0.5% DGG respectively, and in A, B, C, the black, grey and light grey represent the high shear rate (100/s) at 25° C., the low shear rate (0.1/s) at 34° C. before mixing, and the low shear rate (0.1/s) at 34° C. after mixing respectively. D, E, F show the viscosity of compositions (Δη1 value) with 0.1% DGG, 0.3% DGG, 0.5% DGG, respectively.

By comparing the viscosity changes and sample properties before and after adding the simulating nasal fluid (SNF), it can be concluded that PVP-I indeed improved the sample viscosity before and after mixing with the simulating nasal fluid (SNF). In the following examples, we select 0.5% and 0.8% as the appropriate PVP-I concentrations in the compositions, but the viscosity of these two compositions decreased after the addition of simulating nasal fluid (SNF). So it was necessary to change the NaCl concentration to optimize the sample viscosity. Based on viscosity changes, compositions in Italic were excluded for not forming a gel in-situ; whereas the compositions in Bold are the preferred compositions as they were potential good in-situ gel forming compositions.

TABLE 3

Sample Viscosity Determination Results

|  | DGG | PVP-I | pH | η (Pa·s, Before Mixing) 25° C. | η (Pa·s, Before Mixing) 34° C. | η (Pa·s, After Mixing) 34° C. | Δη1 (Pa·s) | Δη2 (Pa·s) |
|---|---|---|---|---|---|---|---|---|
| Composition 1 | 0.1% | 0% | — | 0.006 | 0.021 | 0.233 | 0.227 | 0.212 |
|  |  | *0.2%* | *4.70* | *0.098* | *7.137* | *0.946* | *0.848* | *−6.191* |
|  |  | 0.5% | 4.83 | 0.053 | 0.160 | 1.637 | 1.584 | 1.477 |
|  |  | 0.8% | 4.58 | 0.052 | 0.133 | 0.970 | 0.918 | 0.837 |
|  |  | 1.0% | 4.49 | 0.047 | 0.146 | 0.398 | 0.351 | 0.252 |
| Composition 2 | 0.3% | 0% | — | 0.007 | 0.261 | 0.469 | 0.462 | 0.208 |
|  |  | *0.2%* | *5.01* | *0.143* | *9.566* | *2.780* | *2.637* | *−6.786* |
|  |  | 0.5% | 4.71 | 0.101 | 3.172 | 1.610 | 1.509 | −1.562 |
|  |  | 0.8% | 4.51 | 0.103 | 3.298 | 1.855 | 1.752 | −1.443 |
|  |  | 1.0% | 4.98 | 0.087 | 1.480 | 1.052 | 0.965 | −0.428 |
| Composition 3 | 0.5% | 0% | — | 0.019 | 0.653 | 0.564 | 0.545 | −0.089 |
|  |  | *0.2%* | *4.28* | *0.244* | *33.162* | *23.700* | *23.456* | *−9.462* |
|  |  | *0.5%* | *4.38* | *0.151* | *10.518* | *4.564* | *4.413* | *−5.954* |
|  |  | *0.8%* | *4.38* | *0.195* | *29.399* | *9.805* | *9.610* | *−19.5937* |
|  |  | *1.0%* | *4.27* | *0.173* | *11.795* | *1.788* | *1.615* | *−10.007* |
| Composition 4 | 0% | 0.5% | — | 0.004 | 0.035 | 0.028 | 0.024 | −0.07 |
|  |  | 0.8% | — | 0.004 | 0.025 | 0.027 | 0.023 | 0.002 |

TABLE 4

Sample Property

|  | DGG | PVP-I | Before Mixing | After Mixing | Description |
|---|---|---|---|---|---|
| Composition 1 | 0.1% | 0.2% | Chunks, Good fluidity | Great fluidity | The fluidity is slightly higher, and chunks cause higher viscosity |
|  |  | 0.5% | Great fluidity | Forming thick gel after long time, has thixotropy | Good results, but NaCl amount can still be fine-tuned |
|  |  | 0.8% | Great fluidity | Forming thick gel after long time, has thixotropy | Good results, but NaCl amount can still be fine-tuned |
|  |  | 1.0% | Small chunks, Good fluidity | Forming thick gel after long time, has thixotropy | Chunks before adding simulating liquid, Not suitable for spraying |
| Composition 2 | 0.3% | 0.2% | Forming thick gel at resting, flow slowly under upside-down | Small chunks, good fluidity | Excessive viscosity before adding simulating fluid, Can't spary |
|  |  | 0.5% | Great fluidity | Small chunks, good fluidity | The fluidity is slightly higher after adding simulating liquid, Can be achieved by adjusting salt concentration |

TABLE 4-continued

| | DGG | PVP-I | Before Mixing | After Mixing | Description |
|---|---|---|---|---|---|
| | | 0.8% | Great fluidity | Small chunks, good fluidity | The fluidity is slightly higher after adding simulating liquid, Can be achieved by adjusting salt concentration |
| | | 1.0% | Small chunks, Good fluidity | Small chunks, good fluidity | Chunks, non-uniform |
| Composition 3 | 0.5% | 0.2% | Chunks, good fluidity | Small chunks, good fluidity | Chunks, non-uniform |
| | | 0.5% | Forming thick gel after long time, flow slowly under upside-down, has thixotropy | Forming thick gel at resting, not flow under upside-down | Suitable viscosity |
| | | 0.8% | Forming thick gel at resting, not flow under upside-down | Forming thick gel after long time, flow slowly under upside-down, has thixotropy | Viscosity too high |
| | | 1.0% | Forming thick gel at resting, flow slowly under upside-down, has thixotropy | Small chunks, Good fluidity | Viscosity too high |

Example 2

Formulation Screening of DGG and NaCl Amount in the Formulations

The weighted micronized budesonide and glycerin were fully mixed, 2% PVP-I solution and pure water were added to the total sample weight without gellan gum weight. 1% gellan gum solution was added to the total weight under stirring. pH was adjusted to 4-5.5 with tromethamine and hydrochloric acid. Mother liquor of each group was prepared according to the compositions shown in Table 5 (without NaCl), and 50 μL of NaCl solutions of different concentrations were added into 2 mL mother liquor to make the final concentration of NaCl in the compositions in the range of 0%-0.6%. Sample solutions with different concentrations of NaCl are shown in Table 6.

TABLE 5

| | Composition Details | | | | | |
|---|---|---|---|---|---|---|
| | Budesonide (w/w) | PVP-I (w/w) | Glycerin (w/w) | Gellan Gum (w/w) | NaCl (w/w) | Tromethamine |
| Composition 1 | 0.064% | 0.5% | 2.3% | 0.1% | 0% | pH adjusted to 4-5.5 |
| | | | | | 0.1% | |
| | | | | | 0.2% | |
| | | | | | 0.3% | |
| | | | | | 0.4% | |
| | | | | | 0.5% | |
| | | | | | 0.6% | |
| Composition 2 | 0.064% | 0.5% | 2.3% | 0.3% | 0% | |
| | | | | | 0.1% | |
| | | | | | 0.2% | |
| | | | | | 0.3% | |
| | | | | | 0.4% | |
| Composition 3 | 0.064% | 0.5% | 2.3% | 0.5% | 0% | |
| | | | | | 0.0125% | |
| | | | | | 0.025% | |
| | | | | | 0.05% | |
| | | | | | 0.1% | |
| | | | | | 0.2% | |

TABLE 6

Exemplary Compositions

| | Budesonide (w/w) | PVP-I (w/w) | Glycerin (w/w) | Gellan Gum (w/w) | NaCl (w/w) | Tromethamine |
|---|---|---|---|---|---|---|
| Composition 1 | 0.064% | 0.8% | 2.3% | 0.1% | 0% | pH adjusted to 4-5.5 |
| | | | | | 0.1% | |
| | | | | | 0.2% | |
| | | | | | 0.3% | |
| | | | | | 0.4% | |
| | | | | | 0.5% | |
| | | | | | 0.6% | |
| Composition 2 | 0.064% | 0.8% | 2.3% | 0.3% | 0% | |
| | | | | | 0.1% | |
| | | | | | 0.2% | |
| | | | | | 0.3% | |
| | | | | | 0.4% | |
| | | | | | 0.5% | |
| | | | | | 0.6% | |
| Composition 3 | 0.064% | 0.8% | 2.3% | 0.5% | 0% | |
| | | | | | 0.0125% | |
| | | | | | 0.025% | |
| | | | | | 0.05% | |
| | | | | | 0.2% | |
| | | | | | 0.3% | |
| | | | | | 1.0% | |

The sample viscosity before and after mixing with the SNF was determined at a high shear rate (100/s) at 25° C. and a low shear rate (0.1/s) at 34° C. This was to simulate the change of viscosity before and after the sample was sprayed into the nasal cavity, and to compare the sample spray ability and the gel forming ability when in contact with the SNF. The difference between the sample viscosity of the low shear rate (0.1/s) at 34° C. after mixing with SNF and the sample viscosity of the high shear rate (100/s) at 25° C. was label as Δη1 (Pa·s); and the difference between the sample viscosity of the low shear rate (0.1/s) at 34° C. after mixing with SNF and the sample viscosity of the low shear rate (0.1/s) at 34° C. was labeled as Δη2 (Pa·s). The time of 50 μL of sample (before and after mixing with SNF) flowing from 12 mL tick line to 1.5 mL tick line of a vertically placed 15 mL centrifuge tube was measured. (Compositions in Bold indicate as more suitable formulations)

TABLE 7

0.5% PVP-I Formulation Viscosity Determination Results

| | DGG | NaCl | pH | η (Pa · s, Before Mixing) 25 °C. | η (Pa · s, Before Mixing) 34° C. | η (Pa · s, After Mixing) 34° C. | Δη1 (Pa · s) | Δη2 (Pa · s) |
|---|---|---|---|---|---|---|---|---|
| Composition 1 | 0.1% | 0.4% | 5.43 | 0.00519 | 0.07627 | 0.11883 | 0.11364 | 0.04256 |
| | | 0.5% | | 0.00617 | 0.19224 | 0.07582 | 0.06965 | −0.11642 |
| | | 0.6% | | 0.00495 | 0.08665 | 0.06260 | 0.05765 | −0.02405 |
| Composition 2 | 0.3% | 0.1% | 5.13 | 0.00766 | 0.01790 | 0.15148 | 0.14382 | 0.13358 |
| | | 0.2% | | 0.00643 | 0.09261 | 0.15981 | 0.15338 | 0.0672 |
| | | 0.3% | | 0.00873 | 1.44935 | 0.31878 | 0.31005 | −1.13057 |
| | | 0.4% | | 0.00938 | 0.40252 | 0.11154 | 0.10216 | −0.29098 |
| Composition 3 | 0.5% | 0% | 5.31 | 0.00501 | 0.03544 | 0.35788 | 0.35287 | 0.32244 |
| | | 0.0125% | | 0.00543 | 0.08996 | 0.50804 | 0.50261 | 0.41808 |
| | | 0.025% | | 0.00540 | 0.08276 | 0.36793 | 0.36253 | 0.28517 |
| | | 0.05% | | 0.00858 | 0.07613 | 0.66964 | 0.66106 | 0.59351 |
| | | 0.1% | | 0.01059 | 0.23505 | 0.90038 | 0.88979 | 0.66533 |
| | | 0.2% | | 0.01067 | 1.21323 | 0.69363 | 0.68296 | −0.5196 |

TABLE 8

Properties of Compositions Containing 0.5% PVP-I

| | DGG | NaCl | Before Mixing | After Mixing | Description |
|---|---|---|---|---|---|
| Composition 1 | 0.1% | 0% | Flow, drug precipitation after overnight | Flow | Did not form gel after mixing with SNF. As such, compositions containing 0.1% DGG were not |
| | | 0.1% | Flow, drug precipitation after overnight | Small chunks | |

TABLE 8-continued

Properties of Compositions Containing 0.5% PVP-I

|  | DGG | NaCl | Before Mixing | After Mixing | Description |
|---|---|---|---|---|---|
|  |  | 0.2% | Flow, drug precipitation after overnight | Small chunks | suitable. |
|  |  | 0.3% | Flow | Small chunks |  |
|  |  | 0.4% | Flow, forming gel overnight, flow upside-down | Small chunks |  |
|  |  | 0.5% | Contain some chunks, no after shaking, forming gel after overnight | Small chunks |  |
|  |  | 0.6% | Gel, no chunks after shaking | Small chunks |  |
| Composition 2 | 0.3% | 0% | Flow, drug precipitation | Increased viscosity | Insufficient viscosity |
|  |  | 0.1% | Flow | Gel, flow after shaking | Insufficient viscosity before mixing |
|  |  | 0.2% | Viscous, forming gel after overnight, viscous after shaking | Gel, flow after shaking | Can be suitable composition |
|  |  | 0.3% | Gel, flow after shaking, high viscosity | Flow | Insufficient viscosity after mixing |
|  |  | 0.4% | Gel, flow after shaking, high viscosity | Flow | Insufficient viscosity after mixing |
| Composition 3 | 0.5% | 0% | Flow, large viscosity | Thick, high viscosity | Insufficient viscosity before mixing |
|  |  | 0.0125% | Flow | Gel, flow after shaking | Insufficient viscosity before mixing |
|  |  | 0.025% | Flow, forming gel overnight | Gel, flow after shaking | Can be suitable composition |
|  |  | 0.05% | Thick, flow, forming gel overnight | Gel, flow after shaking | Can be suitable composition |
|  |  | 0.1% | Gel, flow after shaking | Gel, flow after shaking | Can be suitable composition |
|  |  | 0.2% | Gel, flow after shaking | Gel, flow after shaking, high viscosity | Too much viscosity before mixing |

TABLE 9

Viscosity of Compositions Containing 0.8% PVP-I

|  | DGG | NaCl | pH | $\eta$ (Pa·s, Before Mixing) 25° C. | $\eta$ (Pa·s, Before Mixing) 34° C. | $\eta$ (Pa·s, After Mixing) 34° C. | $\Delta\eta1$ (Pa·s) | $\Delta\eta2$ (Pa·s) |
|---|---|---|---|---|---|---|---|---|
| Formulation 1 | 0.1% | 0.3% | 4.41 | 0.00478 | 0.12200 | 0.18428 | 0.1795 | 0.06228 |
|  |  | 0.4% |  | 0.00555 | 0.27444 | 0.15386 | 0.14831 | −0.12058 |
|  |  | 0.5% |  | 0.00537 | 0.09926 | 0.11102 | 0.10565 | 0.01176 |
| Formulation 2 | 0.3% | 0.1% | 4.55 | 0.00875 | 0.10316 | 0.44371 | 0.43496 | 0.34055 |
|  |  | 0.2% |  | 0.00994 | 1.58392 | 0.45995 | 0.45001 | 4.12397 |
|  |  | 0.3% |  | 0.01674 | 0.97332 | 0.19825 | 0.18151 | −0.77507 |
| Formulation 3 | 0.5% | 0.025% | 4.41 | 0.01240 | 0.17028 | 0.47948 | 0.46708 | 0.3092 |
|  |  | 0.05% |  | 0.01489 | 0.24068 | 0.57058 | 0.55569 | 0.3299 |
|  |  | 0.1% |  | 0.01305 | 0.48852 | 0.27943 | 0.26638 | −0.20909 |

TABLE 10

Properties of Compositions Containing 0.8% PVP-I

|  | DGG | NaCl | Before Mixing | After Mixing | Description |
|---|---|---|---|---|---|
| Composition 1 | 0.1% | 0.1% | Flow | Gel, strength less than compositions 2 & 3 | Low viscosity before mixing |
|  |  | 0.2% | Flow | Gel, strength less than compositions 2 & 3 | Low viscosity before mixing |

TABLE 10-continued

Properties of Compositions Containing 0.8% PVP-I

|  | DGG | NaCl | Before Mixing | After Mixing | Description |
|---|---|---|---|---|---|
|  |  | 0.3% | Flow, forming gel overnight | Gel, strength less than compositions 2 & 3 | Can be suitable Composition |
|  |  | 0.4% | Flow, forming gel overnight | Gel, strength less than compositions 2 & 3 | Can be suitable Composition |
|  |  | 0.5% | Flow, forming gel overnight | Gel, strength less than compositions 2 & 3 | Can be suitable Composition |
|  |  | 0.6% | Flow | Gel, strength less than compositions 2 & 3 | Insufficient viscosity before mixing |
| Composition 2 | 0.3% | 0.1% | Flow, forming gel overnight | Gel | Can be suitable Composition |
|  |  | 0.2% | Gel, flow after shaking | Gel | Can be suitable Composition |
|  |  | 0.3% | Gel, flow after shaking | Gel | Can be suitable Composition |
|  |  | 0.4% | Gel, viscous after shaking | Gel | Viscosity too high before mixing |
|  |  | 0.5% | Gel, viscous after shaking | Gel | Viscosity too high before mixing |
|  |  | 0.6% | Flow, chunks | Flow, chunks | Non-uniform before mixing |
| Composition 3 | 0.5% | 0.0125% | Flow, slightly viscous overnight | Gel | Insufficient viscosity before mixing |
|  |  | 0.025% | Flow, forming gel overnight | Gel | Can be suitable composition |
|  |  | 0.05% | Flow, forming gel overnight | Gel | Can be suitable composition |
|  |  | 0.1% | Gel, flow after shaking, large viscosity | Gel | Viscosity too high before mixing |
|  |  | 0.2% | Gel | Gel | Viscosity too high before mixing |
|  |  | 0.3% | Gel | Gel | Viscosity too high before mixing |

FIG. 2 shows gel-forming condition of different compositions (all containing 0.8% PVP-I) with different concentrations of DGG, before and after mixing with SNF. For the compositions containing 0.1% DGG and 0.3% DGG, from left to right, the pictures show results with 0.1%-0.6% NaCl. For the compositions containing 0.5% DGG, the pictures from left to right show results with 0.0125-0.3% of NaCl.

FIG. 3 shows the physical states of the compositions containing 0.8% PVP-I after shaking (A: 0.3% DGG, B: 0.5% DGG).

FIG. 4 shows the viscosity of compositions containing 0.5% PVP-I with different NaCl concentrations (1 represents viscosity determination at 25° C. and 100 s$^{-1}$; 2 represents viscosity determination at 34° C. and 0.1 s$^{-1}$; and 3 represents viscosity determination after mixing with SNF at 34° C., 0.1 s$^{-1}$).

FIG. 5 shows the viscosity of compositions containing 0.8% PVP-I with different NaCl concentrations (1 represents viscosity determination at 25° C. and 100 s$^{-1}$; 2 represents viscosity determination at 34° C. and 0.1 s$^{-1}$; and 3 represents viscosity determination after mixing with SNF at 34° C., 0.1 s$^{-1}$).

By comparing the viscosity changes and composition properties before and after mixing with the simulating nasal fluid (SNF), the compositions were optimized in accordance with the formulations listed in Table 12, and the viscosity increased after adding the simulating nasal fluid (SNF), and the viscosity is appropriate before mixing. Select two groups to do a distribution experiment. (Marked in Bold)

TABLE 12

Composition Optimization

| PVP-I | DGG | NaCl |
|---|---|---|
| 0.5% | 0.3% | 0.2% |
|  | 0.5% | 0.025% |
|  |  | 0.05% |
|  |  | 0.1% |
| 0.8% | 0.1% | 0.3% |
|  |  | 0.4% |
|  |  | 0.5% |
|  | 0.3% | 0.1% |
|  |  | 0.2% |
|  |  | 0.3% |
|  | 0.5% | 0.025% |
|  |  | 0.05% |
|  |  | 0.1% |

Examples 3

Composition-Viscosity Curve Investigation

| Ingredient | Composition 1 | Composition 2 | Composition 3 |
|---|---|---|---|
| Budesonide | 0.064%(w/w) | 0.064%(w/w) | 0.064%(w/w) |
| Povidone Iodine | 0.8%(w/w) | 0.8%(w/w) | 0.8%(w/w) |
| Deacetylated Gellan Gum | 0.3%(w/w) | 0.3%(w/w) | 0.3%(w/w) |

-continued

| Ingredient | Composition 1 | Composition 2 | Composition 3 |
|---|---|---|---|
| Sodium Chloride | 0.1%(w/w) | 0.15%(w/w) | 0.2%(w/w) |
| Glycerin | 2.3%(w/w) | 2.3%(w/w) | 2.3%(w/w) |
| 0.5M Tris Aqueous Solution | Adjust pH to 4-5.5 | Adjust pH to 4-5.5 | Adjust pH to 4-5.5 |
| Ultra-pure Water | — | — | — |

The purpose of this study is to investigate how different NaCl concentrations in the formulations change the samples gelling property.

Process

1) Solution Preparations

Solution 1 (1.0% DGG solution):

29.7 g ultra-pure water was added into a 50 mL beaker; then 0.3 g DGG was slowly added DGG into the beaker under stirring to disperse. The solution was then put into a 90° C. water bath, stirred for 1 hour to let gellan gum solution fully swell. After 1 hour, stirring was stopped, the beaker was taken out from water bath, kept stirring to cool the solution at room temperature (25° C.), then stopped stirring. This solution was labeled as Solution 1.

Solution 2 (2% Povidone Iodine Aqueous Solution):

2% povidone iodine aqueous solution need to be prepared when Solution 1 start to cool down.

39.2 g ultra-pure water was put into a 50 mL beaker, and the beaker was placed on a magnetic stirrer to start stirring at constant speed. And 0.8 g povidone iodine was slowly added into beaker under stirring, and stirred at constant rate for about 10 minutes. This solution was labelled as Solution 2.

Solution 3

Micronized budesonide 0.064 g, glycerin 2.3 g and sodium chloride 0.1 g or 0.15 g or 0.20 g, were all put into a 100 mL beaker, and fully mixed to get Solution 3.

Solution 4

Solution 2 was slowly added into Solution 3 under stirring. After dispersed evenly, add 25 g ultra-pure water, stir until mixed well. And add cooled Solution 1, stir until mixed well. Then use 0.5M Tris aqueous solution to adjust pH to 4-5.5, mixed well, add ultra-pure water to total weight is 100 g, use as the final solution.

Test Method 1.1 Test Conditions:

1.1.1 Sample test condition before mixing with SNF: Initial Temperature: 25° C., temperature Increase Velocity: 2° C./min, final temperature: 34° C.; Shear Rate: 0.1/S; GAP: 1000 μm 1.1.2 Sample test condition after mixing with SNF: Constant Temperature: 34° C.; Shear Rate: 0.1/S; GAP: 1000 um Results:

In addition to the results summary in Table 13 below, FIG. 6-11 also show the viscosity changes of various compositions over a period of time, before or after mixing with a NaCl solution. Specifically, FIG. 6 shows the viscosity of composition 1 over a period of time, before mixing with 0.1% NaCl; FIG. 7 shows the viscosity of composition 2, over a period of time, before mixing with 0.15% NaCl; FIG. 8 shows the viscosity of composition 3 over a period of time, before mixing with 0.2% NaCl; FIG. 9 shows the viscosity of composition 1 over a period of time, after mixing with 0.1% NaCl; FIG. 10 shows the viscosity of composition 2, over a period of time, after mixing with 0.15% NaCl; and FIG. 11 shows the viscosity of composition 3 over a period of time, after mixing with 0.2% NaCl.

TABLE 13

Test Data

| | Before Mixing | After Mixing | Note |
|---|---|---|---|
| Viscosity | Temperature Gradient (25° C.~34° C.) Pa · s | Constant Temperature (34° C.) Pa · s | Viscosity of sample after mixing shows a slowly decreasing trend |
| Composition 1 | 4.50293 to 2.53447 | 6.78432 | |
| Composition 2 | 4.18520 to 2.55655 | 12.3283 | |
| Composition 3 | 5.84848 to 8.73697 | 9.85096 | |

Conclusions

The compositions with 0.1% NaCl and 0.15% NaCl showed a slowly decreasing trend in solution viscosity curve before mixing. This phenomenon is consistent with the property of DGG, which is, as the temperature increases, the viscosity will decrease. While the compositions containing 0.2% NaCl violated this phenomenon, which is, as the temperature increases, the viscosity will also increase. As such, compositions with 0.2% NaCl can be regarded as one of the patent innovations as in-situ gel-forming compositions. Also it was surprisingly discovered that the compositions are both ion sensitive and temperature sensitive.

The viscosity data of the composition containing 0.15% NaCl before mixing at around 34° C. and after mixing showed the suddenly viscosity increasing, from 2.55655 Pa.s to 12.3283 Pa.s, which means gel forming possibility. The viscosity data of the 0.2% NaCl composition before mixing at around 34° C. and after mixing shows the slightly viscosity increasing, i.e., from 8.73697 Pa.s to 9.85096. In other words, after mixing, the final viscosity of the composition containing 0.15% NaCl was slightly higher than the final viscosity of 0.2% NaCl formulation. But the final viscosities of these two formulations are relatively high, which can meet sustained release requirement.

Example 4

Preparation of PVP-I, Fluticasone Proprionate Suspension, 1.0 mg

Budesonide suspensions with PVP-I concentration ranging from about 0.8% by weight were prepared as set forth herein. As a non-limiting example, a composition was prepared using approximately 0.8% PVP-I, and combining with micronized fluticasone proprionate (0.064%), glycerin (2.3%), DGG (0.25%), sodium chloride (0.2%), and purified water; tromethamine/HCl was added to adjust the pH to a target in the range of 4-6. The isotonic mixture was delivered a total daily dose of 1.0 mg fluticasone proprionate via sinonasal spray when completely administered in one day.

Example 5

Preparation of PVP-I, Mometasone Suspension, 1.0 mg

Budesonide suspensions with PVP-I concentration ranging from about 0.8% by weight were prepared as set forth herein. By way of a non-limiting example, a composition was prepared using approximately 0.8% PVP-I product, and combining with micronized micronized mometasone 0.064%, glycerin 2.3%, DGG 0.25%, sodium chloride 0.2%, and purified water; tromethamine/HCl is added to adjust the pH to a target of 4-6. The isotonic mixture was delivered a total daily dose of 1.0 mg fluticasone proprionate via sinonasal spray when completely administered in one day.

Example 6

Antimicrobial Activity of PVP-I Preserved Steroid Solutions

By way of a non-limiting example, PVP-I Preserved Steroid Solutions were prepared according to methods described in Examples 1-5. These solutions were then tested for in-vitro microbiological activity. Microbiological activity can be tested for antimicrobial activity against, for example, bacteria found in the mouth (P. gingivalis), or against other bacteria. In another example, killing time tests were conducted with a series of log phase cultures of gram negative and gram positive organisms including Gentamicin resistant Pseudomonas aerouginosa, methicillin-resistant staph aureus, E. coli, chlamydia trachoma and selected viruses including adenoviruses and rhinoviruses. Controls used may include steroid preparations of commercially available antimicrobial products. Bacterial samples were taken at 30 seconds, 1, 2, 5, 10 and 15 minutes and transferred into culture media containing inactivators for iodine. Similarly, virus killing time tests were sampled at one minute and transferred into inactivating media. The results obtained with the experimental samples were compared with the control samples to assess the level of antimicrobial activity of a composition of the invention.

Example 7

Antimicrobial Preservative Effectiveness Test of PVP-I In Nasal Steroid Preparations By way of a non-limiting example, PVP-I Preserved Steroid Solutions were prepared according to the methods described in Examples 1-5. These solutions were then tested for preservative effectiveness according to standard procedures described in the United States Pharmacopeia, General Chapter 51. The iodophor preservatives as prepared in Examples 1-5 were employed in such a way as to satisfy all requirements for preservative effectiveness also as described in the United States Pharmacopeia, General Chapter 51

Example 8

Chlorhexidine Extended Release In Situ Gel Forming Formulations

The in-situ gel forming chlorhexidine digluconate compositions can be formulated with one or more ion-activated in-situ gel forming materials. The polymeric in-situ gel forming agents may include but are not limited to dextrans, polyethylene glycols, polyvinylpyrolidone, polysaccharide gels, Gelrite®, alginate, sodium alginate, sodium hyaluronate, hyaluronic acid, cellulosic polymers like hydroxypropyl methylcellulose, and carboxy-containing polymers such as polymers or copolymers of acrylic acid, as well as other polymeric demulcents. One or more in-situ gel formation agents can be selected in the compositions. Preferred polymeric in-situ gel forming agents can be Deacetylated gellan gum) (Gelrite®).

Example 9

Radioactive Distribution Experiment

According to Table 13, micronized budesonide and glycerin were fully mixed, and added to this mixture was gellan gum, and then pure water, to prepare a 2 mL formulation. 60 μL radioactive PVP-$I^{125}$ (2 mg/mL) was added into 90 μL of PVP-I free sample and mixed by pipetting to prepare a radioactive composition of this invention.

SD rats (about 160 g) were intramuscularly injected with 2% pentobarbital 400 μL for anesthesia. 10 μL of the radioactive composition thus made was administered into the right nostril, and the radionuclide $I^{125}$ distribution at 0, 0.5, 1, 2, 3, 4, 5, 6, 8 hrs was photographed after administration by gamma camera, and calibrated with 10 μL sample.

TABLE 14

| | Compositions without PVP-$I^{125}$ | | |
|---|---|---|---|
| | Composition 1 (0.1% DGG, 0.4% NaCl) | Composition 2 (0.3% DGG, 0.2% NaCl) | Composition 3-Control (0.2% NaCl) |
| Budesonide | 2.13 mg | 2.13 mg | 2.13 mg |
| Glycerin | 0.077 g | 0.077 g | 0.077 g |
| 1% DGG | 0.333 g | 1 g | 0 g |
| NaCl | 13.4 mg | 6.7 mg | 6.7 mg |
| Water | Add to 2 g | Add to 2 g | Add to 2 g |

Gamma Camera Quantitative Results: The sample groups and control group $I^{125}$ nasal cavity residual rates were calculated and results listed in Table 15. FIG. 12 is drawn from the data in Table 15 and shows the samples and control group $I^{125}$ nasal cavity residual rate distribution-time curve (statistical result: 0.1% DGG and control, , P<0.01; 0.3% DGG and control, *, P<0.001).

TABLE 15

Signal strength ratio of rat nasal to 10 μL calibration sample at different time (%)

| | 0.1% DGG-0.4% NaCl | | | 0.3% DGG-0.2% NaCl | | | Control-0.2% NaCl | |
|---|---|---|---|---|---|---|---|---|
| 0 | 100 | 100 | 100 | 100 | 100 | 100 | 100 | 100 |
| 0.5 | 59.76 | 77.86 | 67.32 | 80.04 | 80.47 | 82.44 | 77.09 | 24.03 |
| 1 | 54.24 | 45.19 | 32.07 | 43.09 | 68.67 | 69.23 | 59.9 | 19.51 |
| 2 | 44 | 33.34 | 28.35 | 30.83 | 65.04 | 29.29 | 32.24 | 9.48 |
| 3 | 39.07 | 37.91 | 30.68 | 40.19 | 71.21 | 15.07 | 26.13 | 9.93 |
| 4 | 35.12 | 24.49 | 21.71 | 31.38 | 65.2 | 11.49 | 19.54 | 6.45 |
| 5 | 35.49 | 20.48 | 17.33 | 25.67 | 61.33 | 12.14 | 12.47 | 0 |
| 6 | 33.57 | 22.85 | 18.58 | 28.51 | 54.34 | 11.13 | 9.34 | 0 |
| 8 | 7.53 | 7.32 | 12.7 | 10.66 | 23.85 | 6.09 | 1.27 | 0.32 |

FIG. 13 shows gamma camera distribution results, in which 1, 2, and 3 represents Compositions 1, 2, and 3, respectively. In group 3, the second rat had no obvious signal which may be attributed to some composition being erupted and fluidity being too strong for retention and being directly swallowed when the composition was administered.

Radioactive $I^{125}$ nasal cavity distribution studies showed that the rat nasal cavity retention capacity was 0.3% DGG group>0.1% DGG group>no DGG group, and the results were statistically different. As such, the composition with 0.3% DGG was better than the composition with 0.1% DGG, and was used for the release experiment.

Examples 10

In Vitro Dissolution Experiment 4 mL of a composition of this invention (containing 0.3% DGG, 0.2% NaCl, 0.8% and PVP-I) was placed in a 14 KDa dialysis bag which was then put into 100 mL SNF pre-warmed to 34.5° C. The composition was shaken with a water bath shaker at 100 rpm. 50 mL release medium was taken out at certain time point (0.5, 1, 1.5, 2, 2.5, 3, 3.5, 4, 4.5, 5, 6 h), and add same volume of release medium (pre-warm to 34.5° C.) quickly. Determine available iodine concentration by sodium thiosulfate titration (0.01M), and using the volume of sodium thiosulfate solution consumed at titration end point to calculate its accumulative release amount, (n=3). The accumulated release rate test results are shown below as Table 16. FIG. 14 shows the data in Table 16 as accumulated release curves.

TABLE 16

| | Accumulated release rate (%) | | | | | |
|---|---|---|---|---|---|---|
| Time | 0.3% DGG-0.2% NaCl | | | Control-0.2% NaCl | | |
| 0.5 | 17.43 | 17.34 | 17.3 | 18.06 | 18.24 | 18.19 |
| 1 | 26.05 | 26.1 | 26.21 | 36.46 | 30.19 | 36.45 |
| 1.5 | 43.59 | 37.87 | 34.6 | 40.75 | 56.5 | 46.33 |
| 2 | 47.87 | 48.06 | 43.35 | 65.77 | 65.37 | 69.6 |
| 2.5 | 56.35 | 54.76 | 51.28 | 74.81 | 73.32 | 75.85 |
| 3 | 65.41 | 63.95 | 60.49 | 87.84 | 84.13 | 87.75 |
| 3.5 | 73.97 | 72.55 | 67.88 | 93.01 | 91.61 | 93.65 |
| 4 | 82.79 | 81.13 | 77.28 | 101.88 | 100.13 | 103.13 |
| 4.5 | 91.55 | 90.36 | 86.14 | 107.68 | 106.39 | 109.01 |
| 5 | 99.75 | 99.2 | 95.31 | 100.29 | 117.95 | 116.38 |
| 6 | 108.4 | 107.69 | 100.43 | | | |

The results showed that the release rate of the composition containing 0.3% DGG was slower than the control group. It also had a sustained release effect and continuously released for 6 hours.

Optimization of Compositions

Sample preparation process: According to the compositions listed in Table 16, micronized budesonide and glycerin were fully mixed, and 2% PVP-I solution and NaCl were then added to the mixture, before pure water was added to the mixture without gellan gum. A 1% gellan gum solution was then added to the mixture under stirring, and then the pH of the composition was adjusted to a value in the range of 4-5.5 with tromethamine and hydrochloric acid. Table 17 lists the final compositions.

TABLE 17

| | Compositions | | | | | |
|---|---|---|---|---|---|---|
| | Budesonide (w/w) | PVP-I (w/w) | Glycerin (w/w) | Gellan Gum (w/w) | NaCl (w/w) | Tromethamine |
| Formulation | 0.064% | 0.8% | 2.3% | 0.3% | 0.2% | Adjust pH |
| 100 g Formulation Amount (add water to 14 g before adding gellan gum) | 64 mg | 2% PVP-I mother liquor 40 g | 2.3 g | 1% gellan gum mother liquor 30 g | 200 mg | to 4-5.5 |

Example 11

Stability Study

According to the preparation methods described above, a 500 g sample solution was prepared, and divided into 50 bottles for 10 g per bottle. The bottles were then placed in a constant temperature and humidity chamber of 25±2° C., RH 60%±5%, set 0 days, 3 days, 7 days and 10 days as time points for stability tests. Table 18 lists the results of the test results.

TABLE 18

Stability test result

|  | Property | pH | Viscosity pa·s (Before Mixing) 25° C.; Shear Rate 100/s | Viscosity pa·s (Before Mixing) 34° C.; Shear Rate 0.1/s | Viscosity pa·s (After Mixing) 34° C.; Shear Rate 0.1/s | PVP-I % | Budesonide % |
| --- | --- | --- | --- | --- | --- | --- | --- |
| 0 Day | Red-brown Clear Liquid | 4.67 | 0.063 0.058 AV:0.061 | 17.32 15.84 AV:16.58 | 5.38 6.95 AV:6.13 | 96.28 96.28 AV:96.28 RSD:0 | 112.50 113.97 AV:113.23 RSD:0.92% |
| 3 Day | Red-brown Clear Liquid | 4.58 | 0.036 0.048 AV:0.042 | 12.39 14.66 AV:13.52 | 1.21 1.76 AV:1.48 | 96.28 96.28 AV:96.28 RSD:0 | 116.20 116.52 AV:116.36 RSD:0.19% |
| 7 Day | Red-brown Clear Liquid | 4.51 | 0.056 0.055 AV:0.056 | 17.26 20.55 AV:18.91 | 9.83 9.96 AV:9.89 | 94.95 94.95 AV:94.95 RSD:0 | 116.34 116.34 AV:116.34 RSD:0 |
| 10 Day | Red-brown Clear Liquid | 4.45 | 0.053 0.055 AV:0.054 | 11.43 15.62 AV:13.52 | 18.45 15.26 AV:16.86 | 94.95 94.95 AV:94.95 RSD:0 | 113.44 112.13 AV:112.78 RSD:0.82% |

The results show that the composition used in this test had chunks, that PVP-I and budesonide were very stable in the composition, and the composition was very stable at the pH level of 4.60 over a 10-day test period.

Example 12

In Vitro Anti-Bacterial and Anti-Fungal Biofilm Studies

To study the in vitro effect of a composition of this invention on established biofilms of *Staphylococcus aureus*, *Psuedomonas aeruginosa* and *Candida Albicans*, these biofilms were developed on solid surfaces in separate conical tubes from tryptic soy broth or Sabouraud's dextrose agar inoculated with desired organism. After incubation, biofilms were recovered and enumerated. Each solid-surface biofilm was then challenged with a composition of this invention or a sterile saline control. Following neutralization, all samples were recovered and enumerated. The average post-exposure log reduction vs. sterile saline control in viable *Pseudomonas aeruginosa* and *Staphylococcus aureus* recovered from a treated biofilm and the average post-exposure log reduction vs. saline control in viable *C. Albicans* recovered from a treated biofilm were measured to be at least 3 log reduction (over 99.9% kill) in in-vitro studies of eliminating established biofilms of fungus (*C. albicans*) and bacteria of both *Staphylococcus aureus* and *Pseudomonas aeruginosa* after 10 minutes with the compositions of this invention.

Example 13

Antibacterial Study

A composition of this invention, a Marketed drug (Budesonide Nasal Spray (AstraZeneca plc, Batch: VAXA) and a self-made control blank matrix.
 1. Preparation of Test Samples
   2.1, Following Example 3 Process for a composition of this invention.
   2.2, Self-made control drug-free matrix Solution 1 (1% DGG solution):

29.7 g ultra-pure water was added into a 50 mL beaker, then 0.3 g DGG, and DGG was slowly added into the beaker under stirring until it dispersed. The solution was then put into a 90° C. water bath, stirred for 1 hour to let gellan gum solution fully swell. After 1 hour, stirring was stopped and the beaker was taken out from the water bath, stirring was resume to cool the solution to the room temperature (25° C.) before stirring was stopped. This solution was used as Solution 1.

Solution 2:

2.3 g glycerin and 0.20 g sodium chloride were put into a 100 mL beaker, and fully mixed to get Solution 2.

Solution 3:

40 g ultra-pure water was added into Solution 2 slowly under stirring. After dispersed evenly, additional 25 g ultra-pure water was added, and the mixture is stirred until mixed well. Cooled Solution 1 was added and the mixture was stirred until it was mixed well. A certain amount of 0.5 M Tris aqueous was added and mixed well before ultra-pure water was added to the final total weight of 100 g. The resultant solution was used as the final solution in test.

3. Test Method and Result 3.1 Test Method

Anti-microbial Efficacy Test was conducted based on the Pharmacopoeia of People's Republic of China, 2015, Volume IV, General Rule 1121, which is incorporated herein by reference. The steps are described in the following table:

| | |
|---|---|
| Sample and Blank Matrix Inoculation | 1: Take 2 sterilized 250 mL blue cap bottle, which are labeled as No.1 and No.2, respectively; add 100 mL test sample, then add respectively:<br>No. 1: 1 mL *Staphylococcus Aureus* solution (Concentration: $10^7$-$10^8$ cfu/ml)<br>No.2: 1 mL *Pseudomonas Aeruginosa* solution (Concentration: $10^7$-$10^8$ cfu/mL)<br>2: Each bottle of test sample is vigorously stirred via sterilized glass rod, to let test bacteria uniformly distribute in the test sample<br>3: After complete stirring, stored in thermostat incubator at 20-25° C. in the dark |
| Original Drug Inoculation | 1: Take 2 original drug, which are labeled as No.1 and No.2, respectively after removing aluminum cap then add respectively:<br>No. 1: 0.06 mL *Staphylococcus Aureus* solution (Concentration: $10^8$-$10^9$ cfu/ml)<br>No.2 : 0.06 mL *Pseudomonas Aeruginosa* solution (Concentration: $10^8$-$10^9$ cfu/ml)<br>2: Aftet inoculation, use sealing film to seal spray pump and vial and cover with a protective cap<br>3: Gently shake the bottle, to mix bacteria solution and test sample<br>4: Store in thermostat incubator at 20-25° C. in the dark |
| Sample Examine Method | 1: Plate method: 1:10 test solution, buffer is pH 7.0 sterile sodium chloride-peptone buffer containing 0.05% (ml/ml) polysorbate 80<br>2: Sample prepare: take test sample 1 ml, add the pH 7.0 sterile sodium chloride-peptone buffer containing 0.05% (ml/ml) polysorbate 80 to total 10 ml, as 1:10 test solution |
| Examine Time Point | On the second day, take 1 mL of test sample from No.1 and No.2 container, and measure bacterial bacteria number contained in each test sample |

| Acceptable | | Reduced Ig Value Day | | | |
|---|---|---|---|---|---|
| Standard | | 2 | 7 | 14 | 28 |
| | Bacterial A | 2 | 3 | / | NI |
| | Fungus A | / | / | 2 | NI |

Note:

NI (Not Increased) means that the test bacteria increased amount does not exceed 0.5 lg compared with the previous measurement time.

"A" means the anti-microbial efficacy standard was achieved.

In special cases, like the antiseptic mayincrease the side effects, the efficacy at least met the "B" standard.

Results:

*Staphylococcus Aureus*: After inoculation with the composition of this invention as described above, the original drug, and the drug-free blank matrix, the initial concentration of three biofilm samples were all $1.06 \times 10^7$ cfu/mL. On the second day of the anti-microbial efficacy test, a sample from each group was taken to examine according to the above-mentioned test method, and bacterial number of each sample were less than 10 cfu/mL for group treated with the tested composition of this invention, 60 cfu/mL for the group tested with the original drug, and not countable for the drug-free blank matrix, with the Ig reduction value being 7.0, 5.2, and 0, respectively. The results show that the tested composition of this invention and the original drug both qualified for the antibacterial activity on *Staphylococcus aureus*, as they both had strong anti-bacterial efficacy, while the tested composition of this invention being much more potent and efficacious than the original drug, and the drug-free blank matrix had no inhibitory effect on *Staphylococcus aureus*.

TABLE 19

*Staphylococcus Aureus*

| Name | Batch | Initial Concentration (cfu/ml) | 2-Day Count | $Log_{10}$ Reduction |
|---|---|---|---|---|
| Compound Nasal Spray | 180808 | $1.06 \times 10^7$ | <10 | 7.0 |
| Budesonide Nsal Spray (AstraZeneca plc) | VAXA | | 110 | 5.0 |
| Compound Nasal Spray Blank Matrix | — | | Uncountable | 0 |

According to Pharmacopoeia of People's Republic of China, 2015, Volume IV, General Rule 1121, Antimicrobial Efficacy Test Method

*Pseudomonas Aeruginosa*: After inoculation with a test composition of this invention, an original drug, and a drug-free blank matrix, the initial concentration of three biofilm samples were all 0.74×10$^7$ cfu/mL. On the second day of anti-microbial efficacy test, a sample of each biofilm was taken for examination according to the above-mentioned test method, and the bacterial number in each biofilm sample was 20 cfu/mL for the one treated with the composition, 10 cfu/mL for the one treated with the original drug, and not countable for a drug-free blank matrix, with the Ig reduction values being 5.6, 5.9, and 0, respectively. The results show that both the tested composition of this invention and the original drug both qualified for the antibacterial activity on *Pseudomonas aeruginosa*, as they both had strong anti-bacterial efficacy with the test composition of this invention showing stronger anti-bacterial efficacy, and the drug-free blank matrix had no inhibitory effect on *Pseudomonas aeruginosa*.

TABLE 20

*Pseudomonas Aeruginosa*

| Name | Batch | Initial Concentration (cfu/ml) | 2-Day Count | Log$_{10}$ Reduction |
|---|---|---|---|---|
| Compound Nasal Spray | 180808 | 0.74 × 10$^7$ | 20 | 5.6 |
| Budesonide Nsal Spray (AstraZeneca plc) | VAXA | | 10 | 5.9 |
| Compound Nasal Spray Blank Matrix | — | | Uncountable | 0 |

According to Pharmacopoeia of People's Republic of China, 2015, Volume IV, General Rule 1121, Antimicrobial Efficacy Test Method Examples 14

Sedimentation Ratio Test

1. Method

TABLE 22

| Ingredient | Formulation 3 |
|---|---|
| Budesonide | 0.064% (w/w) |
| Povidone Iodine | 0.8% (w/w) |
| Deacetylated Gellan Gum (DGG) | 0.3% (w/w) |
| Sodium Chloride | 0.2% (w/w) |
| Glycerin | 2.3% (w/w) |
| 0.5M Tris Aqueous Solution | Adjust pH to 4-5.5 |
| Ultra-pure Water | — |

1) Sample Solution Preparation

Reference Examples 3 Process

2) Control Solution Preparation (No DGG)

Solution 1 (2% Povidone Iodine Aqueous Solution)

39.2 g ultra-pure water was added into a 50 mL beaker which was then placed on a magnetic stirrer for stirring at a constant speed. 0.8 g povidone iodine was then slowly added into the beaker with stirring at a constant stirring rate for about 10 minutes. This solution was used as Solution 1.

Solution 2:

0.064 g micronized budesonide, 2.3 g glycerin and 0.20 g sodium chloride were all put into a 100 mL beaker, and fully mixed to get Solution 2.

Solution 3:

Solution 1 was slowly added into Solution 2 with stirring until it was dispersed evenly. 55 g ultra-pure water was then added to the mixture, and stirred until mixed well. 0.5 M Tris aqueous solution was used to adjust the pH to a target in the range of 4-5.5 and the mixture was mixed well, before ultra-pure water was added to reach a total weight of 100 g. This solution was used as the final solution.

Data

The Sedimentation Ratio Test Method as provided in the Pharmacopoeia of People's Republic of China, 2015, Volume IV, General Rule 0105 (which is incorporated herein by reference) was used for the test herein.

Sedimentation Ratio: The suspension eye drops (except the eye drops containing fine powder) were examined by the following method, the sedimentation ratio should not be less than 0.90.

Examine Protocol: Unless otherwise specified, 50 mL of test sample was retrieve with a mixing cylinder with stopper tightly plugged and the sample was shaken vigorously for 1 minute. The starting height ($H_O$) of the suspension was measured, and the suspension was allowed to stand for 3 hours before the final height H of suspension was recorded. Sedimentation Ratio ($H/H_O$) was calculated as follows:

TABLE 23

| Time | Sample Solution | Control Solution | Note |
|---|---|---|---|
| 0 h | $H_0$ = 13.90 cm | $H_0$ = 14.0 cm | The control solution almost |
| 3 h | $H_1$ = 13.80 cm | $H_1$ = 2.0 cm | completely sinks at 3 h, |
| 5 h | $H_2$ = 13.80 cm | $H_2$ = 2.0 cm | but the sample solution |
| 8 h | $H_3$ = 13.80 cm | $H_3$ = 2.0 cm | almost maintains |
| 24 h | $H_4$ = 13.80 cm | $H_4$ = 2.0 cm | the initial height at 24 h. |

Results and Conclusions

TABLE 24

| Time | Sample Solution- Sedimentation Ratio | Sample Solution- Sedimentation Ratio |
|---|---|---|
| 3 h | 0.99 | 0.14 |
| 5 h | 0.99 | 0.14 |
| 8 h | 0.99 | 0.14 |
| 24 h | 0.99 | 0.14 |

Conclusion: The sample biofilm solution showed almost no sedimentation after 24 hours, which was much larger than the limit specified by the pharmacopoeia, indicating that the physical stability of the system was very good; the blank control without DGG almost sank to the bottom of cylinder after 3 hours. The sedimentation ratio was lower than 0.90, which did not reach the limit prescribed by the pharmacopoeia, indicating that the sample solution formulation meets the requirement of sedimentation ratio, and was much higher than the limit prescribed by the pharmacopoeia, the stability cycle is long, which greatly increased the physical stability of the solution system.

Examples 15

Other Gel Matrix Screenings

1. Experiment Process

A certain amount of sodium chloride was slowly and evenly added into 85 g ultra-pure water under stirring until it dissolved. The gel forming agent was then slowly and evenly added into the solution under stirring until it was dispersed. The solution was then put into a 90° C. water bath, stirred for 1 hour to fully swell. The solution was then cooled to the room temperature. Povidone iodine was slowly added into the solution with stirring to completely dissolve. An aqueous Tris-Hcl solution (0.5 mol/L) was added to the solution to adjust its pH to about 5.5 and then the solution was stirred evenly, before water was added to give the total weight of 100 g.

TABLE 25

| Sodium Alginate Matrix | | |
| --- | --- | --- |
| Sodium Alginate | Sodium Chloride | Povidone Iodine |
| 0.1% | 0.2% | 0.5% |
| | | 0.8% |
| | 0.3% | 0.5% |
| | | 0.8% |
| 0.3% | 0.2% | 0.5% |
| | | 0.8% |
| | 0.3% | 0.5% |
| | | 0.8% |

TABLE 26

| Carrageenan Matrix | | |
| --- | --- | --- |
| Carrageenan | Sodium Chloride | Povidone Iodine |
| 0.1% | 0.2% | 0.5% |
| | | 0.8% |
| | 0.3% | 0.5% |
| | | 0.8% |
| 0.3% | 0.2% | 0.5% |
| | | 0.8% |
| | 0.3% | 0.5% |
| | | 0.8% |

TABLE 27

| Xanthan Matrix | | |
| --- | --- | --- |
| Xanthan | Sodium Chloride | Povidone Iodine |
| 0.1% | 0.2% | 0.5% |
| | | 0.8% |
| | 0.3% | 0.5% |
| | | 0.8% |
| 0.3% | 0.2% | 0.5% |
| | | 0.8% |
| | 0.3% | 0.5% |
| | | 0.8% |

2. The test results are summarized in the following tables.

Sodium Alginate Result

TABLE 28

| Composition 1 | | Test Result | | | |
| --- | --- | --- | --- | --- | --- |
| Povidone Iodine | 0.5 g | pH | Viscosity (initial) | Viscosity (Mixing) | Note |
| Sodium Alginate 80A | 0.1 g | Before mixing: 3.40; After mixing: 5.56 | 83.18-0 mp · s | 111.14-0 mp · s | Almost no viscosity |
| Sodium Chloride | 0.2 g | | | | |
| Tris-Hcl (0.5M/pH8.8) | 0.45 ml | | | | |
| Ultra-pure Water | Add to 100 g | | | | |

TABLE 29

| Composition 2 | | Test Result | | | |
| --- | --- | --- | --- | --- | --- |
| Povidone Iodine | 0.8 g | pH | Viscosity (initial) | Viscosity (Mixing) | Note |
| Sodium Alginate 80A | 0.1 g | Before mixing: 3.15; After mixing: 5.44 | 108.91-0 mp · s | 50.1-0 mp · s | Almost no viscosity |
| Sodium Chloride | 0.2 g | | | | |
| Tris-Hcl (0.5M/pH8.8) | 0.83 ml | | | | |
| Ultra-pure Water | Add to 100 g | | | | |

TABLE 30

| Composition 3 | | Test Result | | | |
|---|---|---|---|---|---|
| Povidone Iodine | 0.5 g | pH | Viscosity (initial) | Viscosity (Mixing) | Note |
| Sodium Alginate 80A | 0.1 g | Before mixing: 3.42; After mixing: 5.48 | 75.25-0 mp · s | 102.15-0 mp · s | Almost no viscosity |
| Sodium Chloride | 0.3 g | | | | |
| Tris-Hcl (0.5M/pH8.8) | 0.45 ml | | | | |
| Ultra-pure Water | Add to 100 g | | | | |

TABLE 31

| Composition 4 | | Test Result | | | |
|---|---|---|---|---|---|
| Povidone Iodine | 0.8 g | pH | Viscosity (initial) | Viscosity (Mixing) | Note |
| Sodium Alginate 80A | 0.1 g | Before mixing: 3.09; After mixing: 5.41 | 70.82-0 mp · s | 113.30-0 mp · s | Almost no viscosity |
| Sodium Chloride | 0.3 g | | | | |
| Tris-Hcl (0.5M/pH8.8) | 0.84 ml | | | | |
| Ultra-pure Water | Add to 100 g | | | | |

TABLE 32

| Composition 5 | | Test Result | | | |
|---|---|---|---|---|---|
| Povidone Iodine | 0.5 g | pH | Viscosity (initial) | Viscosity (Mixing) | Note |
| Sodium Alginate 80A | 0.3 g | Before mixing: 4.03; After mixing: 5.42 | 60.79-14.08 mp · s | 16.67-0 mp · s | Almost no viscosity |
| Sodium Chloride | 0.2 g | | | | |
| Tris-Hcl (0.5M/pH8.8) | 0.48 ml | | | | |
| Ultra-pure Water | Add to 100 g | | | | |

TABLE 33

| Composition 6 | | Test Result | | | |
|---|---|---|---|---|---|
| Povidone Iodine | 0.8 g | pH | Viscosity (initial) | Viscosity (Mixing) | Note |
| Sodium Alginate 80A | 0.3 g | Before mixing: 3.84; After mixing: 5.51 | 95.12-14.40 mp · s | 18.55-0 mp · s | Almost no viscosity |
| Sodium Chloride | 0.2 g | | | | |
| Tris-Hcl (0.5M/pH8.8) | 0.825 ml | | | | |
| Ultra-pure Water | Add to 100 g | | | | |

TABLE 34

| Composition 7 | | Test Result | | | |
|---|---|---|---|---|---|
| Povidone Iodine | 0.5 g | pH | Viscosity (initial) | Viscosity (Mixing) | Note |
| Sodium Alginate 80A | 0.3 g | Before mixing: 3.93; After mixing: 5.60 | 73.27-18.15 mp · s | 0-0 mp · s | Almost no viscosity |
| Sodium Chloride | 0.3 g | | | | |
| Tris-Hcl (0.5M/pH8.8) | 0.48 ml | | | | |
| Ultra-pure Water | Add to 100 g | | | | |

TABLE 35

| Composition 8 | | Test Result | | | |
|---|---|---|---|---|---|
| Povidone Iodine | 0.8 g | pH | Viscosity (initial) | Viscosity (Mixing) | Note |
| Sodium Alginate 80A | 0.3 g | Before mixing: 3.68; After mixing: 5.60 | 39.37-14.27 mp·s | 14.96-0 mp·s | Almost no viscosity |
| Sodium Chloride | 0.3 g | | | | |
| Tris-Hcl (0.5M/pH8.8) | 0.83 ml | | | | |
| Ultra-pure Water | Add to 100 g | | | | |

Xanthan Result

TABLE 36

| Composition 9 | | Test Result | | | |
|---|---|---|---|---|---|
| Povidone Iodine | 0.5 g | pH | Viscosity (initial) | Viscosity (Mixing) | Note |
| Xanthan | 0.1 g | Before mixing: 2.80; After mixing: 5.58 | 118.16-20.14 mp·s | 109.63-13.52 mp·s | Almost no viscosity |
| Sodium Chloride | 0.2 g | | | | |
| Tris-Hcl (0.5M/pH8.8) | 0.54 ml | | | | |
| Ultra-pure Water | Add to 100 g | | | | |

TABLE 37

| Composition 10 | | Test Result | | | |
|---|---|---|---|---|---|
| Povidone Iodine | 0.8 g | pH | Viscosity (initial) | Viscosity (Mixing) | Note |
| Xanthan | 0.1 g | Before mixing: 2.56; After mixing: 5.60 | 114.05-20.66 mp.s | 101.97-13.64 mp.s | Almost no viscosity |
| Sodium Chloride | 0.2 g | | | | |
| Tris-Hcl (0.5M/pH 8.8) | 0.83 ml | | | | |
| Ultra-pure Water | Add to 100 g | | | | |

TABLE 38

| Composition 11 | | Test Result | | | |
|---|---|---|---|---|---|
| Povidone Iodine | 0.5 g | pH | Viscosity (initial) | Viscosity (Mixing) | Note |
| Xanthan | 0.1 g | Before mixing: 2.82; After mixing: 5.45 | 100.57-18.43 mp.s | 79.09-0 mp.s | Almost no viscosity |
| Sodium Chloride | 0.3 g | | | | |
| Tris-Hcl (0.5M/pH 8.8) | 0.52 ml | | | | |
| Ultra-pure Water | Add to 100 g | | | | |

TABLE 39

| Composition 12 | | Test Result | | | |
|---|---|---|---|---|---|
| Povidone Iodine | 0.8 g | pH | Viscosity (initial) | Viscosity (Mixing) | Note |
| Xanthan | 0.1 g | Before mixing: 2.57; After mixing: 5.61 | 105.48-17.11 mp.s | 20.34-0 mp.s | Almost no viscosity |
| Sodium Chloride | 0.3 g | | | | |
| Tris-Hcl (0.5M/pH 8.8) | 0.84 ml | | | | |
| Ultra-pure Water | Add to 100 g | | | | |

TABLE 40

| Composition 13 | | Test Result | | | |
|---|---|---|---|---|---|
| Povidone Iodine | 0.5 g | pH | Viscosity (initial) | Viscosity (Mixing) | Note |
| Xanthan | 0.3 g | Before mixing: 2.96; After mixing: 5.39 | 133.48-79.15 mp.s | 60.53-40.29 mp.s | Almost no viscosity |
| Sodium Chloride | 0.2 g | | | | |
| Tris-Hcl (0.5M/pH 8.8) | 0.58 ml | | | | |
| Ultra-pure Water | Add to 100 g | | | | |

TABLE 41

| Composition 14 | | Test Result | | | |
|---|---|---|---|---|---|
| Povidone Iodine | 0.8 g | pH | Viscosity (initial) | Viscosity (Mixing) | Note |
| Xanthan | 0.3 g | Before mixing: 2.74; | 139.71-71.01 mp.s | 90.94-37.90 mp.s | Almost no viscosity |
| Sodium Chloride | 0.2 g | | | | |
| Tris-Hcl (0.5M/pH 8.8) | 0.85 ml | After mixing: 5.44 | | | |
| Ultra-pure Water | Add to 100 g | | | | |

TABLE 42

| Composition 15 | | Test Result | | | |
|---|---|---|---|---|---|
| Povidone Iodine | 0.5 g | pH | Viscosity (initial) | Viscosity (Mixing) | Note |
| Xanthan | 0.3 g | Before mixing: 2.99; | 141.06-77.31 mp.s | 85.32-39.55 mp.s | Almost no viscosity |
| Sodium Chloride | 0.3 g | | | | |
| Tris-Hcl (0.5M/pH 8.8) | 0.55 ml | After mixing: 5.62 | | | |
| Ultra-pure Water | Add to 100 g | | | | |

TABLE 43

| Composition 16 | | Test Result | | | |
|---|---|---|---|---|---|
| Povidone Iodine | 0.8 g | pH | Viscosity (initial) | Viscosity (Mixing) | Note |
| Xanthan | 0.3 g | Before mixing: 2.80; | 132.61-72.56 mp.s | 74.92-40.09 mp.s | Almost no viscosity |
| Sodium Chloride | 0.3 g | | | | |
| Tris-Hcl (0.5M/pH 8.8) | 0.84 ml | After mixing: 5.56 | | | |
| Ultra-pure Water | Add to 100 g | | | | |

Carrageenan Result

TABLE 44

| Composition 17 | | Test Result | | | |
|---|---|---|---|---|---|
| Povidone Iodine | 0.5 g | pH | Viscosity (initial) | Viscosity (Mixing) | Note |
| Carrageenan | 0.1 g | Before mixing: 2.69; | 86.53-0 mp.s | 104.52-0 mp.s | Almost no viscosity |
| Sodium Chloride | 0.2 g | | | | |
| Tris-Hcl (0.5M/pH 8.8) | 0.55 ml | After mixing: 5.62 | | | |
| Ultra-pure Water | Add to 100 g | | | | |

TABLE 45

| Composition 18 | | Test Result | | | |
|---|---|---|---|---|---|
| Povidone Iodine | 0.8 g | pH | Viscosity (initial) | Viscosity (Mixing) | Note |
| Carrageenan | 0.1 g | Before mixing: 2.50; | 75.32-0 mp.s | 98.35-0 mp.s | Almost no viscosity |
| Sodium Chloride | 0.2 g | | | | |
| Tris-Hcl (0.5M/pH 8.8) | 0.82 ml | After mixing: 5.63 | | | |
| Ultra-pure Water | Add to 100 g | | | | |

TABLE 46

| Composition 19 | | Test Result | | | |
|---|---|---|---|---|---|
| Povidone Iodine | 0.5 g | pH | Viscosity (initial) | Viscosity (Mixing) | Note |
| Carrageenan | 0.1 g | Before mixing: 2.67; | 70.73-0 mp.s | 13.64-0 mp.s | Almost no viscosity |
| Sodium Chloride | 0.3 g | | | | |
| Tris-Hcl (0.5M/pH 8.8) | 0.52 ml | After mixing: 5.60 | | | |
| Ultra-pure Water | Add to 100 g | | | | |

TABLE 47

| Composition 20 | | | Test Result | | |
|---|---|---|---|---|---|
| | | pH | Viscosity (initial) | Viscosity (Mixing) | Note |
| Povidone Iodine | 0.8 g | Before mixing: 2.52; After mixing: 5.49 | 111.30-0 mp.s | 15.59-0 mp.s | Almost no viscosity |
| Carrageenan | 0.1 g | | | | |
| Sodium Chloride | 0.3 g | | | | |
| Tris-Hcl (0.5M/pH 8.8) | 0.79 ml | | | | |
| Ultra-pure Water | Add to 100 g | | | | |

TABLE 48

| Formulation 21 | | | Test Result | | |
|---|---|---|---|---|---|
| | | pH | Viscosity (initial) | Viscosity (Mixing) | Note |
| Povidone Iodine | 0.5 g | Before mixing: 2.77; After mixing: 5.57 | 114.57-0 mp.s | 95.82-0 mp.s | Almost no viscosity |
| Carrageenan | 0.3 g | | | | |
| Sodium Chloride | 0.2 g | | | | |
| Tris-Hcl (0.5M/pH 8.8) | 0.53 ml | | | | |
| Ultra-pure Water | Add to 100 g | | | | |

TABLE 49

| Formulation 22 | | | Test Result | | |
|---|---|---|---|---|---|
| | | pH | Viscosity (initial) | Viscosity (Mixing) | Note |
| Povidone Iodine | 0.8 g | Before mixing: 2.53; After mixing: 5.63 | 121.22-0 mp.s | 98.58-0 mp.s | Almost no viscosity |
| Carrageenan | 0.3 g | | | | |
| Sodium Chloride | 0.2 g | | | | |
| Tris-Hcl (0.5M/pH 8.8) | 0.53 ml | | | | |
| Ultra-pure Water | Add to 100 g | | | | |

TABLE 50

| Formulation 23 | | | Test Result | | |
|---|---|---|---|---|---|
| | | pH | Viscosity (initial) | Viscosity (Mixing) | Note |
| Povidone Iodine | 0.5 g | Before mixing: 2.73; After mixing: 5.48 | 108.35-0 mp.s | 90.85-0 mp.s | Almost no viscosity |
| Carrageenan | 0.3 g | | | | |
| Sodium Chloride | 0.3 g | | | | |
| Tris-Hcl (0.5M/pH 8.8) | 0.52 ml | | | | |
| Ultra-pure Water | 1.00 g | | | | |

TABLE 51

| Formulation 24 | | | Test Result | | |
|---|---|---|---|---|---|
| | | pH | Viscosity (initial) | Viscosity (Mixing) | Note |
| Povidone Iodine | 0.8 g | Before mixing: 2.50; After mixing: 5.41 | 106.52-0 mp.s | 88.25-0 mp.s | Almost no viscosity |
| Carrageenan | 0.3 g | | | | |
| Sodium Chloride | 0.3 g | | | | |
| Tris-Hcl (0.5M/pH 8.8) | 0.86 ml | | | | |
| Ultra-pure Water | Add to 100 g | | | | |

3. Results and Conclusion

None of these three gel matrix showed phase transition property and their viscosity did not increase much, which could not satisfy with improving the physical stability of the suspension. They did not achieve the effect of gel sustained release either.

What is claimed is:

1. An aqueous pharmaceutical composition comprising an antiseptic, a steroid, and a biocompatible polysaccharide as a gel-forming material, wherein the composition can form a gel in situ upon instillation into a sinonasal cavity of a subject in need thereof, the antiseptic comprises povidone-iodine (PVP-I), the steroid comprises mometasone, fluticasone, or budesonide, or a salt, an ester, or any combination thereof, and the polysaccharide comprises deacetylated gellan gum (DGG); wherein the antiseptic is contained in the composition at a concentration of 0.1% to 5.0% (weight/weight or weight/volume), the steroid is contained in the composition at a concentration of 0.02% to 0.1% (weight/weight or weight/volume), and the polysaccharide is contained in the composition at a concentration of 0.1% to 2.0% (weight/weight or weight/volume).

2. The aqueous pharmaceutical composition of claim 1, wherein the antiseptic is contained in the composition at a concentration of 0.2% to 1.0% (weight/weight or weight/volume).

3. The aqueous pharmaceutical composition of claim 1, wherein the steroid comprises fluticasone or budesonide, or a salt, an ester, or any combination thereof.

4. The aqueous pharmaceutical composition of claim 1, wherein the polysaccharide further comprises xanthan, sodium alginate, or carrageenan.

5. The aqueous pharmaceutical composition of claim 1, wherein the polysaccharide is contained in the composition at a concentration of 0.1% to 0.5% (weight/weight).

6. The aqueous pharmaceutical composition of claim 1, further comprises an osmotic pressure regulator, a surfactant, a viscosity increasing agent, a pH regulator, or a cooling agent.

7. The aqueous pharmaceutical composition of claim 6, wherein the osmotic pressure regulator comprises sodium chloride, glycerol, polyethylene glycol 400 (PEG400), mannitol, or boric acid.

8. The aqueous pharmaceutical composition of claim 7, wherein the osmotic pressure regulator is contained in the composition at a concentration of 0.1 to 0.5% (weight/volume).

9. The aqueous pharmaceutical composition of claim 6, wherein the surfactant comprises polysorbate-20, polysorbate-60, polysorbate-80, polyoxyethylene surfactant, polyxoypropylene surfactant, cyclodextrin, tyloxapol, PEG 35 Caster oil, glycerin, or polyoxyl 40 Strerate.

10. The aqueous pharmaceutical composition of claim 9, wherein the surfactant is contained in the composition at a concentration of 0.01%-2% (weight/weight).

11. The aqueous pharmaceutical composition of claim 6, wherein the viscosity increasing agent comprises polyvinyl alcohol, polyvinylpyrrolidone, methyl cellulose, hydroxypropylmethylcellulose, hydroxyethylcellulose, carboxymethylcellulose, hydroxypropylcellulose, microcrystalline cellulose, carboxymethyl cellulose sodium, or dextrose anhydrous.

12. The aqueous pharmaceutical composition of claim 11, wherein the viscosity increasing agent is contained in the composition at a concentration of 0.01%-2% (weight/weight).

13. The aqueous pharmaceutical composition of claim 6, wherein the cooling agent comprises a menthol, a methone glycerin acetyl, a menthyl ester, a carboxamide, a menthane glycerol ketal, an alkyl substituted urea, a sulfonamide, a terpene analog, franone, a phosphine oxide, a derivative thereof, a camphor, or a bonel.

14. The aqueous pharmaceutical composition of claim 6, wherein the pH regulator comprises sodium hydroxide, tris(hydroxymethyl)aminomethane (Tris), phosphoric acid, or any mixture thereof.

15. The aqueous pharmaceutical composition of claim 1, wherein the composition has a pH value in the range of 4.0 to 7.0.

16. The aqueous pharmaceutical composition of claim 1, wherein the composition has a pH value in the range of 4.0 to 6.0.

17. The aqueous pharmaceutical composition of claim 1, further comprises an anesthetic agent.

18. The aqueous pharmaceutical composition of claim 1, wherein the composition is in the form of a solution, a suspension, or an emulsion.

19. The aqueous pharmaceutical composition of claim 18, wherein the solution is a gel forming aqueous solution, or gel forming suspension.

20. The aqueous pharmaceutical composition of claim 1, wherein water is added to form a solution ready for use in irrigation or spraying into the sinal cavity of the subject.

21. A method for treating a clinical sinus symptom of an airway of a subject in need thereof, comprising administering to a sinal cavity of the subject an aqueous pharmaceutical composition comprising an antiseptic, a steroid, and a biocompatible polysaccharide, wherein the composition can form a gel in situ upon instillation into the sinal cavity, wherein the antiseptic comprises povidone-iodine (PVP-I), the steroid comprises mometasone, fluticasone, or budesonide, or a salt, an ester, or any combination thereof, and the polysaccharide comprises deacetylated gellan gum (DGG); wherein the antiseptic is contained in the composition at a concentration of 0.1% to 5.0% (weight/weight or weight/volume), the steroid is contained in the composition at a concentration of 0.02% to 0.1% (weight/weight or weight/volume), and the polysaccharide is contained in the composition at a concentration of 0.1% to 2.0% (weight/weight or weight/volume).

22. The method of claim 21, wherein the sinus symptom is inflammation, infection, formation of biofilm, rhinosinusitis, congestion, pain, pressure, fatigue, or thickened nasal discharge.

23. The method of claim 21, wherein the airway is sinus, nose, or lung.

24. The method of claim 21, wherein the pharmaceutical composition is administered to the subject by a rinsing bottle, metered-dose, manual-pump spray, a metering, or an atomizing spray pump.

25. The method of claim 21, wherein the steroid comprises budesonide, micronized fluticasone proprionate, or micronized mometasone.

26. The method of claim 21, wherein the dose volume of the antiseptic administered to the subject is between about 10 mcg to about 300 mcg per day, about 20 mcg to about 200 mcg per day, about 30 mcg to about 100 mcg per day, or about 50 mcg per day with two sprays per nostril per day.

27. A method for improving a lung condition of a cystic fibrosis patient, comprising washing a sinal cavity of the patient with an aqueous pharmaceutical composition comprising an antiseptic, a steroid, and a biocompatible polysaccharide, wherein the composition can form a gel in situ upon instillation into the sinal cavity, wherein the antiseptic comprises povidone-iodine (PVP-I), the steroid comprises mometasone, fluticasone, or budesonide, or a salt, an ester, or any combination thereof, and the polysaccharide comprises deacetylated gellan gum (DGG); wherein the antiseptic is contained in the composition at a concentration of 0.1% to 5.0% (weight/weight or weight/volume), the steroid is contained in the composition at a concentration of 0.02% to 0.1% (weight/weight or weight/volume), and the polysaccharide is contained in the composition at a concentration of 0.1% to 2.0% (weight/weight or weight/volume).

28. The method of claim 27, wherein the steroid comprises micronized budesonide, micronized fluticasone proprionate, or micronized mometasone.

* * * * *